US012055543B2

(12) United States Patent
Fotouhi et al.

(10) Patent No.: US 12,055,543 B2
(45) Date of Patent: Aug. 6, 2024

(54) METHODS AND DEVICES FOR DETECTION OF THC

(71) Applicant: Graphene-DX, Inc., Boston, MA (US)

(72) Inventors: Mohammed Fotouhi, Weston, MA (US); Mehdi Abedi, Brighton, MA (US); Edward Alvin Greenfield, Stoughton, MA (US); Reza Mollaaghababa, Natick, MA (US); Mohammad E. Taslim, Needham, MA (US)

(73) Assignee: Graphene-DX, Inc., Boston, MA (US)

( * ) Notice: Subject to any disclaimer, the term of this patent is extended or adjusted under 35 U.S.C. 154(b) by 495 days.

(21) Appl. No.: 16/846,224

(22) Filed: Apr. 10, 2020

(65) Prior Publication Data

US 2020/0300845 A1    Sep. 24, 2020

Related U.S. Application Data

(63) Continuation-in-part of application No. 16/422,743, filed on May 24, 2019.
(Continued)

(51) Int. Cl.
*G01N 33/543* (2006.01)
*G01N 33/94* (2006.01)

(52) U.S. Cl.
CPC ......... *G01N 33/5438* (2013.01); *G01N 33/94* (2013.01)

(58) Field of Classification Search
CPC ... G01N 33/5438; G01N 33/94; G01N 33/948
See application file for complete search history.

(56) References Cited

U.S. PATENT DOCUMENTS

| 4,983,102 A | 1/1991 | Swain |
| 6,037,168 A | 3/2000 | Brown |
(Continued)

FOREIGN PATENT DOCUMENTS

| CA | 2971589 A1 | 6/2016 |
| DE | 19600521 A1 | 7/1996 |
(Continued)

OTHER PUBLICATIONS

Renaud-Young, Margaret, et al. "Development of an ultra-sensitive electrochemical sensor for Δ9-tetrahydrocannabinol (THC) and its metabolites using carbon paper electrodes." Electrochimica Acta 307 (2019): 351-359. (Year: 2019).*
(Continued)

*Primary Examiner* — Robert J Eom
(74) *Attorney, Agent, or Firm* — Potomac Law Group, PLLC; John J. Penny, Jr.

(57) ABSTRACT

In one aspect, a method of detecting tetrahydrocannabinol (THC) in a sample is disclosed, which comprises bringing the sample into contact with a graphene layer functionalized with an antibody exhibiting specific binding to THC, applying a time-varying electric field to said antibody-functionalized graphene layer, monitoring electrical resistance of said graphene layer in response to interaction with said sample, and detecting presence of THC in the sample by detecting a change in said electrical resistance indicative of interaction of THC with said anti-body functionalized graphene layer.

24 Claims, 12 Drawing Sheets

Related U.S. Application Data

(60) Provisional application No. 62/832,264, filed on Apr. 10, 2019, provisional application No. 62/676,079, filed on May 24, 2018.

(56) References Cited

U.S. PATENT DOCUMENTS

| | | | |
|---|---|---|---|
| 8,575,663 | B2 | 11/2013 | Lieber et al. |
| 8,695,810 | B2 | 4/2014 | Gao |
| 8,907,384 | B2 | 12/2014 | Pace et al. |
| 9,146,209 | B2 | 9/2015 | Johnson et al. |
| 9,160,024 | B1 | 10/2015 | Moore et al. |
| 9,162,885 | B2 | 10/2015 | Lee et al. |
| 9,612,240 | B2 | 4/2017 | Johnson, Jr. et al. |
| 9,618,476 | B2 | 4/2017 | Goldsmith |
| 9,664,674 | B2 | 5/2017 | Taslim et al. |
| 9,735,366 | B2 | 8/2017 | Turchanin |
| 9,765,395 | B2 | 9/2017 | Goldsmith |
| 9,857,328 | B2 | 1/2018 | Hoffman |
| 9,859,394 | B2 | 1/2018 | Hoffman et al. |
| 9,887,352 | B2 | 2/2018 | Bessonov et al. |
| 10,168,297 | B2 | 1/2019 | Johnson, Jr. et al. |
| 10,401,352 | B2 | 9/2019 | Taslim et al. |
| 10,429,342 | B2 | 10/2019 | Hoffman et al. |
| 10,429,381 | B2 | 10/2019 | Hoffman |
| 10,607,989 | B2 | 3/2020 | Hoffman |
| 10,660,697 | B2 | 5/2020 | Xiao et al. |
| 10,751,986 | B2 | 8/2020 | Lerner et al. |
| 10,758,303 | B2 | 9/2020 | Xiao et al. |
| 10,782,285 | B2 | 9/2020 | Taslim et al. |
| 10,811,539 | B2 | 10/2020 | Van et al. |
| 10,968,481 | B2 | 4/2021 | Van et al. |
| 2004/0146863 | A1 | 7/2004 | Pisharody et al. |
| 2005/0072213 | A1 | 4/2005 | Besnard et al. |
| 2006/0188934 | A1 | 8/2006 | Chang et al. |
| 2008/0017737 | A1 | 1/2008 | So et al. |
| 2009/0092965 | A1 | 4/2009 | Weiss et al. |
| 2009/0311727 | A1 | 12/2009 | Watkins et al. |
| 2010/0222224 | A1 | 9/2010 | Suni et al. |
| 2011/0217763 | A1 | 9/2011 | Rasooly et al. |
| 2012/0129198 | A1 | 5/2012 | Buechler et al. |
| 2012/0156688 | A1 | 6/2012 | McAlpine et al. |
| 2012/0264232 | A1 | 10/2012 | Kramer et al. |
| 2013/0164859 | A1 | 6/2013 | Johnson et al. |
| 2013/0217598 | A1 | 8/2013 | Ludwig et al. |
| 2014/0220617 | A1 | 8/2014 | Yung et al. |
| 2014/0295406 | A1 | 10/2014 | Sundvor et al. |
| 2015/0011020 | A1 | 1/2015 | Sundvor et al. |
| 2015/0065363 | A1 | 3/2015 | Johnson, Jr. et al. |
| 2015/0173883 | A1 | 6/2015 | Ingber et al. |
| 2015/0307936 | A1 | 10/2015 | Goldsmith |
| 2015/0309018 | A1 | 10/2015 | Goldsmith |
| 2015/0346141 | A1 | 12/2015 | Johnson et al. |
| 2016/0025675 | A1 | 1/2016 | Goldsmith |
| 2016/0054312 | A1 | 2/2016 | Goldsmith |
| 2016/0097764 | A1 | 4/2016 | Taslim et al. |
| 2016/0223538 | A1 | 8/2016 | McAlpine et al. |
| 2017/0067888 | A1 | 3/2017 | Taslim et al. |
| 2017/0212116 | A1 | 7/2017 | Braga et al. |
| 2017/0299602 | A1 | 10/2017 | Johnson, Jr. et al. |
| 2017/0307562 | A1 | 10/2017 | Goldsmith |
| 2017/0361599 | A1 | 12/2017 | Lerner et al. |
| 2017/0365474 | A1 | 12/2017 | Pan et al. |
| 2017/0365477 | A1 | 12/2017 | Pan et al. |
| 2017/0365562 | A1 | 12/2017 | Pan et al. |
| 2018/0037952 | A1 | 2/2018 | Goldsmith |
| 2019/0079068 | A1 | 3/2019 | Taslim et al. |
| 2019/0187090 | A1 | 6/2019 | Grabbert et al. |
| 2019/0284615 | A1 | 9/2019 | Fotouhi et al. |
| 2019/0317081 | A1 | 10/2019 | Taslim et al. |
| 2020/0011860 | A1 | 1/2020 | Nawana et al. |
| 2020/0141931 | A1 | 5/2020 | Hoffman et al. |
| 2020/0300845 | A1 | 9/2020 | Fotouhi et al. |
| 2021/0102937 | A1 | 4/2021 | Taslim et al. |

FOREIGN PATENT DOCUMENTS

| | | | |
|---|---|---|---|
| EP | 3149464 | A1 | 4/2017 |
| EP | 3201627 | B1 | 8/2017 |
| EP | 3308153 | A1 | 4/2018 |
| EP | 3344980 | A1 | 7/2018 |
| EP | 3491370 | A1 | 6/2019 |
| EP | 3280822 | B1 | 11/2020 |
| JP | 2005308761 | A | 11/2005 |
| JP | 2016047777 | A | 4/2016 |
| WO | 2001/47704 | A1 | 7/2001 |
| WO | 2014/160861 | A1 | 10/2014 |
| WO | 2017/103269 | A1 | 6/2017 |
| WO | 2017/194746 | A1 | 11/2017 |
| WO | 2018079314 | A1 | 5/2018 |
| WO | WO-2018200794 | A1 * | 11/2018 ............ A61B 5/082 |

OTHER PUBLICATIONS

Eissa, Shimaa, Rema A. Almthen, and Mohammed Zourob. "Disposable electrochemical immunosensor array for the multiplexed detection of the drug metabolites morphine, tetrahydrocannabinol and benzoylecgonine." Microchimica Acta 186.8 (2019): 1-9. (Year: 2019).*

U.S. Appl. No. 17/027,029, filed Sep. 21, 2020, Taslim, et al.

International Preliminary Report on Patentability for Application No. PCT/US2019/34043, mailed Dec. 3, 2020 (9 Pages).

Liu, et al. "An ISFET based sensing array with sensor offset compensation and pH sensitivity enhancement." Proceedings of 2010 IEEE International Symposium on Circuits and Systems. IEEE, pp. 2283-2286. (Year: 2010).

Pandey, et al. "Graphene-interfaced electrical biosensor for label-free and sensitive detection of foodborne pathogenic E. coli 0157: H7." Biosensors and Bioelectronics 91, Dec. 16, 2016: 226-231. (Year: 2016).

Zuo, et al., "A PDMS/paper/glass hybrid microfluidic biochip integrated with aptamer-functionalized graphene oxide nano-biosensors for one-step multiplexed pathogen detection." Lab on a Chip 13.19 (2013): 3921-3928., 18 Pages, (Year: 2013).

U.S. Appl. No. 17/152,513, filed Jan. 19, 2021, Nawana, et al.

U.S. Appl. No. 17/170,439, filed Mar. 20, 2021, Nawana, et al.

European Extended Search Report, 19215320.3, dated Aug. 13, 2020, 9 pages.

M.M. Pereira da Silva Neves et al., "Development of electrochemical immunosensors for celiac disease clinical diagnosos and gluten-free food control", (2012), pp. 202.

Nehra et al., "Current trends in nanomaterial embedded field effect transistor-based biosensor." Biosensors and Bioelectronics 74 (2015), pp. 731-743.

Rani, et al., "Operational of ISFET as a pH sensor by using signal modulated reference electrode." 2009 International Conference on Information and Multimedia Technology. IEEE, (2009), 3 pages.

S. Eissa et al., "Electrochemical immunosensor for the milk allergen beta-lactoglobulin based on electrografting of organic film on graphene modified screen-printed carbon electrodes", Biosensors and Bioelectronics, Elsevier Science Ltd. UK, Amsterdam, NL, vol. 38, No. 1, Jun. 6, 2012 (Jun. 6, 2012), pp. 308-313.

S. Srivastava et al., "Graphene Oxide-Based Biosensor for Food Toxin Detection", Applied Biochemistry and Biotechnology, Humana Press Inc, New York, vol. 174, No. 3, Jun. 11, 2014 (Jun. 11, 2014), pp. 960-970.

Yan, et al., "Solution-Gated Graphene Transistors for Chemical and Biological Sensors." Advanced healthcare materials 3.3 (2014), pp. 313-331.

Kim, K., et al., Presentation "Antibody-Functionalized Carbon Nanotubes in Cancer Therapy," Apr. 28, 2008, pp. 1-72.

Kodali, V.K., et al., "Nonperturbative Chemical Modification of Graphene for Protein Micropatterning," Langmuir (2011), vol. 27, No. (3), pp. 863-865.

Kruss, S., et al., "Neurotransmitter Detection Using Corona Phase Molecular Recognition on Fluorescent Single-Walled Carbon Nanotube Sensors," American Chemical Society J. Am. Chem. Soc. (2014), vol. 136, pp. 713-724.

(56) References Cited

OTHER PUBLICATIONS

Kuzmany, H., et al., "Functionalization of Carbon Nanotubes," Synthetic Metals vol. 141, (2004), pp. 113-122.
Lee, P.P., et al., "Targeting Colorectal Cancer Cells With Single-Walled Carbon Nanotubes Conjugated to Anticancer Agent SN-38 and EGFR Antibody," Biomaterials vol. 34, (2013) pp. 8756-8765.
Lerner, M.B., et al., Presentation Detecting Lyme Disease Using Antibody-Functionalized Single-Walled Carbon Nanotube Transistors, Department of Physics and Astronomy, University of Pennsylvania, 209 South 33rd Street, Philadelphia, PA 19104, (2014).
Li, C., et al., Mass Detection Using Carbon Nanotube-Based Nanomechanical Resonators, Applied Physics Letters vol. 84, No. 25, Jun. 21, 2004, pp. 5246-5248.
Li, R., et al., P-Glycoprotein Antibody Functionalized Carbon Nanotube Overcomes the Multidrug Resistance of Human Leukemia Cells, ACSNANO (2010), vol. 4, No. 3, pp. 1399-1408.
Li, X., et al., Transfer of Large-Area Graphene Films for High-Performance Transparent Conductive Electrodes, NANO Letters, (2009), vol. 9, No. 12, pp. 4359-4363.
Liang, X., et al., "Toward Clean and Crackless Transfer of Graphene," ACSNANO, (2011), vol. 5, No. 11, pp. 9144-9153.
Lillehoj, P.B., et al., Rapid electrochemical detection on a mobile phone. Lab Chip. Aug. 7, 2013;13(15):2950-5. doi: 10.1039/c3lc50306b.
Liu, J., et al., "Visible Light Detection Using Single-Walled Carbon Nanotube Film and Gold Nanoparticles or Nanorods," Journal of Applied Physics, vol. 107, (2010), pp. 1-4.
Ma, P., et al., "Dispersion and Functionalization of Carbon Nanotubes for Polymer-Based Nanocomposites: A Review," Composites: Part A 41 (2010), pp. 1345-1367.
Mairal, T., et al, "Microfluorimeter with disposable polymer chip for detection of coeliac disease toxic gliadin," Lab on a Chip, vol. 9, No. 24, Jan. 1, 2009, pp. 3535-3542.
Mao, S., et al., "Specific Biosensing Using Carbon Nanotubes Functionalized With Gold Nanoparticle—Antibody Conjugates" Carbon, vol. 48 (2010), pp. 479-486.
Mao, S., et al., Graphene-based electronic biosensors. J Mater Res, 2017;32(15):2954-2965.
Marches, R., et al., "Specific Thermal Ablation of Tumor Cells Using Single-Walled Carbon Nanotubes Targeted by Covalently-Coupled Monoclonal Antibodies," Int. J. Cancer: (2009), vol. 125, pp. 2970-2977.
Margolskee, RF., "Molecular Mechanisms of Bitter and Sweet Taste Transduction," The Journal of Biological Chemistry, (Issue of Jan. 4, 2002), vol. 277, No. 1, pp. 1-4.
Maruyama, H., et al., "Evaluation of Thermal Conductivity of Single Carbon Nanotubes in Air and Liquid Using a Fluorescence Temperature Sensor," Applied Physics Letters, 103, (2013), pp. 1-5.
Matsumoto, K. (Ed.), "Frontiers of Graphene and Carbon Nanotubes, Devices and Application," Springer Japan KK Is Part of Springer Science+Business Media (2015), (www.springercom).
McDevitt, MR, et al., "Tumor Targeting With Antibody-Functionalized, Radiolabeled Carbon Nanotubes," The Journal of Nuclear Medicine, (2007), vol. 48, No. 7, pp. 1180-1189.
Menard-Moyon, C., et al., "Functionalized Carbon Nanotubes for Probing and Modulating Molecular Functions," Chemistry & Biology 17, Feb. 26, 2010, pp. 107-115.
Miller, K. et al. "Portable gluten biosensor (Thesis)," University of Arizona, May 31, 2009; pp. FP-45, retrieved Mar. 13, 2018 from <http://hdl.handle.net/10150/192520>.
Moreira, F., et al., "Artificial Antibodies for Troponin T by its Imprinting on the Surface of Multiwalled Carbon Nanotubes: Its Use as Sensory Surfaces," Biosensors and Bioelectronics, vol. 28 (2011) pp. 243-250.
Moreno, M., Analysis of Polyphenols in White Wine by CZE With Amperometric Detection Using Carbon Nanotube-Modified Electrodes, Electrophoresis, (2011), vol. 32, pp. 877-883.
Moron, B., et al., "Sensitive Detection of Cereal Fractions That Are Toxic to Celiac Disease Patients by Using Monoclonal Antibodies to a Main Immunogenic Wheat Peptide1-3," Am J Clin Nutr, (2008), vol. 87 pp. 405-414.
Mulvey. J.J., et al., "Self-Assembly of Carbon Nanotubes and Antibodies on Tumours for Targeted Amplified Delivery," Nature Nanotechnology, (2013), vol. 8, pp. 763-771.
Naguib, N., et al., "Effect of Carbon Nanofibre Structure on the Binding of Antibodies," Nanotechnology, vol. 16, (2005), pp. 567-571.
Nassef, H.M., et al., Electrochemical immunosensor for detection of celiac disease toxic gliadin in foodstuff. Anal Chem. Dec. 1, 2008;80(23):9265-71. doi: 10.1021/ac801620j.
Neves, M.M., et al., An electrochemical deamidated gliadin antibody immunosensor for celiac disease clinical diagnosis. Analyst. Apr. 7, 2013;138(7):1956-8. doi: 10.1039/c3an36728b. Epub Feb. 12, 2013.
Neves, Marta MPS, et al. "Voltammetric immunosensor for the diagnosis of celiac disease based on the quantification of antigliadinantibodies." Sensors and Actuators B: Chemical 163.1 (2012): 253-259.
Orth, RA., et al., "A Comparative Study of the Proteins of Wheats of Diverse Baking Qualities," American Association of Cereal Chemists, Inc., (1972), pp. 268-275.
Pei-Tzu, C., et al, "Detection of Gliadin in Foods Using a Quartz Crystal Microbalance Biosensor That Incorporates Gold Nanoparticles," Journal of Agricultural and Food Chemistry, v. 60, No. 26, Jul. 4, 2012, pp. 6483-6492.
Penza, M., et al., Carbon Nanotube Acoustic and Optical Sensors for Volatile Organic Compound Detection, Nanotechnology, (2005), vol. 16, pp. 2536-2547.
Pham, X.H., et al., "Electrochemical Characterization of a Single-Walled Carbon Nanotube Electrode for Detection of Glucose," Analytica Chimica Acta, (2010), vol. 671, pp. 36-40.
Pilolli, R., et al., "Advances in biosensor development based on integrating nanotechnology and applied to food-allergen management," Trends in Analytical Chemistry, Jun. 1, 2013, v. 47, pp. 12-26.
Plata, D.L., et al., "Thermogravimetry-Mass Spectrometry for Carbon Nanotube Detection in Complex Mixtures," American Chemical Society Environ. Sci. Technol., (2012), vol. 46, pp. 12254-12261.
Pumera, M., et al., Graphene for electrochemical sensing and biosensing. TrAC Trends in Analytical Chemistry, Oct. 2010, vol. 29, Issue 9, pp. 954-965.
Pumera, M., Graphene in biosensing. materialstoday, Jul.-Aug. 2011;14(7-8):308-315.
Qian, Z., et al., "1.27 GHz Graphene-Aluminum Nitride Nano Plate Resonant Infrared Detector," Transducers (2015), Anchorage, Alaska, pp. 1429-1432.
Qian, Z., et al., "245 MHz Graphene-Aluminum Nitride Nano Plate Resonator," Transducers 2013, Barcelona, Spain, (Jun. 16-20, 2013), pp. 2005-2008.
Qian, Z., et al., "Single Transistor Oscillator Based on a Graphene-Aluminum Nitride Nano Plate Resonator," (2013) Joint UFFC, EFTF and PFM Symposium, pp. 559-561.
Qian, Z., et al., Graphene as a Massless Electrode for Ultrahigh-Frequency Piezoelectric Nanoelectromechanical Systems, American Chemical Society Nano Lett. (2015), vol. 15, pp. 4599-4604.
Qian, Z., et al., High Resolution Calorimetric Sensing Based on Aluminum Nitride MEMS Resonant Thermal Detectors, (2014) IEEE, pp. 1-4.
Rajabzade, H., et al., Functionalized Carbon Nanotubes With Gold Nanoparticles to Fabricate a Sensor for Hydrogen Peroxide Determination, E-Journal of Chemistry (2012), vol. 9, No. 4, pp. 2540-2549.
Remaggi, F., et al., "Carbon Nanotube Sensor for Vibrating Molecules," New Journal of Physics vol. 15, (2013) 083016 pp. 1-20.
Resczenski, J., et al., Presentation "Functionalizing Carbon Nanotubes with Antibodies for the Detection of Prostate Cancer Biomarkers," Johnson Group, Sunfest, (2011), pp. 1-14.

(56) References Cited

OTHER PUBLICATIONS

Rotariu, L, et al., "Low Potential Thiocholine Oxidation at Carbon Nanotube-Ionic Liquid Gel Sensor," Sensors and Actuators B 150, (2010) pp. 73-79.
Santavicca, D.F., et al., "Bolometric and Nonbolometric Radio Frequency Detection in a Metallic Single-Walled Carbon Nanotube," Applied Physics Letters, (2011), vol. 98, pp. 1-4.
Shampine, L.F., et al., "Solving Index 1 DAES in Matlab and Simulink," Draft Paper Feb. 22, 1999, pp. 1-15.
U.S. Appl. No. 16/260,773, filed Jan. 19, 2019, Methods and Devices for Detection of Pathogens.
Sharma, D., et al., Insight into the biosensing of graphene oxide: Present and future prospects. Arabian Journal of Chemistry, Mar. 2016;9(2):238-261.
Sirdeshmukh, R., et al., "Functionalization of Carbon Nanotubes with Antibodies for Breast Cancer Detection Applications," Proceedings of the 2004 International Conference on MEMS, NANO and Smart Systems, (2004), IEEE pp. 1-6.
Song, Y., et al., "Carbon Nanotube Volatile Organic Liquid Sensor," Applied Physics Letters 95, (2009), pp. 1-4.
Sousa, C., et al., "Sensitive Detection of Cereal Fractions That Are Toxic to Coeliac Disease Patients, Using Monoclonal Antibodies to a Main Immunogenic Gluten Peptide," Celiac Disease—From Pathophysiology to Advanced Therapies, Department of Microbiology and Parasitology, Faculty of Pharmacy, University of Seville, Seville, Spain, (2008).
Stefansson, S., et al., "Targeting Antibodies to Carbon Nanotube Field Effect Transistors by Pyrene Hydrazide Modification of Heavy Chain Carbohydrates," Journal of Nanotechnology vol. 2012, Article ID 490175, pp. 1-8.
Takeda, S., et al., "Application of Carbon Nanotubes for Detecting Anti-Hemagglutinins Based on Antigen—Antibody Interaction," Biosensors and Bioelectronics, vol. 21 (2005) pp. 201-205.
Tooski, S.B., Sense Toxins/Sewage Gases by Chemically and Biologically Functionalized Single-Walled Carbon Nanotube Sensor Based Microwave Resonator, Journal of Applied Physics, vol. 107, (2010), pp. 1-9.
Tooski, S.B., Functionalized Single Wall Carbon Nanotube Sensor in a Perturbed Microwave Resonant Cavity Based Toxin/Pollutant Gas Pressure Sensor, Journal of Applied Physics, vol. 107, (2010), pp. 1-10.
Tooski, SB, et al., "Optical Properties of Carbon Nanotube Gas Sensor," Journal of Applied Physics, vol. 110, (2011), pp. 1-8.
Varghese, et al. "Recent advances in graphene based gas sensors" Sensors and Actuators; 2015; vol. B 218; pp. 160-183.
Vasilescu, Alina, Alis Vezeanu, and Mihaela Badea. "Electrochemical Impedance Spectroscopy Investigations Focused on Food Allergens." Sensing in Electroanalysis. University Press Centre Pardubice, Czech Republic 59-83.
Venturelli E., et al., "Antibody Covalent Immobilization on Carbon Nanotubes and Assessment of Antigen Binding," Small (2011), vol. 7, No. 15, pp. 2179-2187.
Villamizar, R., et al., "Rapid Detection of Aspergillus Flavus in Rice Using Biofunctionalized Carbon Nanotube Field Effect Transistors," Anal Bioanal Chem, (2011), vol. 399 pp. 119-126.
Vlandas, A., et al., "Enzyme-Free Sugar Sensing in Microfluidic Channels With an Affinity-Based Single-Wall Carbon Nanotube Sensor," Analytical Chemistry, vol. 82, No. 14, (Jul. 15, 2010), pp. 6090-6097.
Volkov, A.N., et al., "Effect of Bending Buckling of Carbon Nanotubes on Thermal Conductivity of Carbon Nanotube Materials," Journal of Applied Physics, vol. 111, (2012) pp. 1-12.
Wang, X., et al., "Transparent, Stretchable, Carbon-Nanotube-Inlaid Conductors Enabled by Standard Replication Technology for Capacitive Pressure, Strain and Touch Sensors†," J. Mater. Chem. A, (2013), vol. 1, pp. 3580-3586.
Wardani, N.I., et al., "Zinc Layered Hydroxide-2(3-Chlorophenoxy) Propionate Modified Multi-Walled Carbon Nanotubes Paste Electrode for the Determination of Nano-Molar Levels Copper (II)," Sensors and Actuators B 198, (2014), pp. 243-248.
Wieser H, "Chemistry of Gluten Proteins," Food Microbiology vol. 24, (2007), pp. 115-119.
Xiao, Y., et al., "Anti-HER2 IgY Antibody-Functionalized Single-Walled Carbon Nanotubes for Detection and Selective Destruction of Breast Cancer Cells," BMC Cancer, 2009, vol. 9 No. 351 pp. 1-11.
Xu, J., et al., "Fabrication of a Magnet-Assisted Alignment Device for the Amperometric Detection of Capillary Electrophoresis Using a Carbon Nanotube/Polypropylene Composite Electrode," Electrophoresis (2013), vol. 34, pp. 2017-2024.
Yang, K., et al., "Preparation and Functionalization of Graphene Nanocomposites for Biomedical Applications," Nature Protocols vol. 8 No. 12, (2013) pp. 2393-2403.
Yang, L, et al., "Carbon Nanotube-Sensor-Integrated Microfluidic Platform for Real-Time Chemical Concentration Detection," Electrophoresis (2009), vol. 30, pp. 3198-3205.
Yun, Y., et al., "A Nanotube Array Immunosensor for Direct Electrochemical Detection of Antigen—Antibody Binding," Sensors and Actuators B vol. 123 (2007) pp. 177-182.
Zhan, et al. "Graphene Field-Effect Transistor and Its Application for Electronic Sensing" Small; 2014; vol. 10; No. 20; pp. 4042-4065.
Zhao, C., et al., "Formation of Uniform Reduced Graphene Oxide Films on Modified PET Substrates Using Dropasting Method," Particuology vol. 17 (2014) pp. 66-73.
[No Author Listed] Agilent Technologies, "Agilent B1500A Semiconductor Device Analyzer User's Guide", Edition 7, Oct. 2008, p. 1-628.
[No Author Listed] Agilent Technologies International sarl, Agilent B1500A Semiconductor Device Analyzer User's Guide, Edition 6, Nov. 2007, p. 1-588.
Asad, M., et al., "Surface Acoustic Wave Based H2S Gas Sensors Incorporating Sensitive Layers of Single Wall Carbon Nanotubes Decorated With Cunanoparticles," Sensors and Actuators B 198 (2014) pp. 134-141.
Balasubramanian, K, et al., "Chemically Functionalized Carbon Nanotubes," Small (2005) vol. 1, No. 2, pp. 180-192.
Bard, A., et al., "Electrochemical Methods, Fundamentals and Applications," Second Edition, John Wiley & Sons, Inc., New York, Copyright (2001) © John Wiley & Sons, Inc. All rights reserved. ISBN 0-471-04372-9, pp. 1-850.
Bhattacharya, M., et al., "Carbon Nanotube Based Sensors for the Detection of Viruses," Sensors and Actuators B 155, (2011), pp. 67-74.
Bianco, A., Presentation Nanotube Functionalization and Therapeutic Applications, Immunologie et Chimie Therapeutiques, CNRS, Strasbourg, France, Nanosoft (Roscoff), May 21-25, 2007, pp. 1-68.
Bietz, J.A., et al., "Identity of High Molecular Weight Gliadin and Ethanol-Soluble Glutenin," Subunits of Wheat: Relation to Gluten Structure, Cereal Chem. (1980), vol. 57, No. 6, pp. 415-421.
Capparelli, R., et al., "Quantification of Gliadin Levels to the Picogram Level by Flow Cytometry," Wiley-Liss, Inc., Cytometry Part A 63A, (2005), pp. 108-113.
Chakravarty, P., et al., "Thermal Ablation of Tumor Cells With Antibody-Functionalized Single-Walled Carbon Nanotubes," PNAS, Jun. 24, (2008), vol. 105, No. 25, pp. 8697-8702.
Chopra, S., et al., "Selective Gas Detection Using a Carbon Nanotube Sensor," Applied Physics Letters, vol. 83, No. 11, Sep. 15, (2003), pp. 2280-2282.
Coyle, B., et al., "Carbon-Binding Designer Proteins That Discriminate Between sp2-and sp3-Hybridized Carbon Surfaces," American Chemical Society, Langmuir, (2013), vol. 29, pp. 4839-4846.
De Gracia Villa, M., et al., "Carbon Nanotube Composite Peptide-Based Biosensors as Putative Diagnostic Tools for Rheumatoid Arthritis," Biosensors and Bioelectronics, (2011), vol. 27 pp. 113-118.
De Leo, F., et al., "Structural and Dynamic Properties of Monoclonal Antibodies Immobilized on CNTs: A Computational Study," Chemistry European Journal, (2013), vol. 19, pp. 12281-12293.
Deng, C., et al., "Electrochemical Detection of Nitrite Based on the Polythionine/Carbon Nanotube Modified Electrode," Thin Solid Films 520, (2012), pp. 7026-7029.

(56) References Cited

OTHER PUBLICATIONS

Desai, S.C., et al., "Hypergolic Fuel Detection Using Individual Single Walled Carbon Nanotube Networks," Journal of Applied Physics, (2010) vol. 107, pp. 114509-1-114509-17.

Didar, T.F., et al., Improved treatment of systemic blood infections using antibiotics with extracorporeal opsonin hemoadsorption. Biomaterials. Oct. 2015;67:382-92. doi: 10.1016/j.biomaterials.2015. 07.046. Epub Jul. 26, 2015.

Drouvalakis, K., et al., Peptide-Coated Nanotube-Based Biosensor for the Detection of Disease-Specific Autoantibodies in Human Serum, Biosensors and Bioelectronics, (2008), vol. 23, pp. 1413-1421.

Efrat, A., et al., Curve Matching, Time Warping, and Light Fields: New Algorithms for Computing Similarity Between Curves, Department of Computer Science, University of Arizona, Suresh Venkatasubramanian, AT&T Labs—Research, (2007), pp. 1-19.

Eissa, S., et al., "A Graphene-Based Electrochemical Competitive Immunosensor for the Sensitive Detection of Okadaic Acid in Shellfish", Nanoscale, (2012), vol. 4, pp. 7593-7599.

Extended European Search Report for Application No. 15846637.5, issued Apr. 3, 2018.

Fadel, T., et al., "Clustering of Stimuli on Single-Walled Carbon Nanotube Bundles Enhances Cellular Activation," Langmuir, (2010), vol. 26 No. 8, pp. 5645-5654.

Fernstrom, J.D., et al., "Mechanisms for Sweetness1-3," The Journal of Nutrition, Supplement May 9, 2012, pp. 1S of 8S.0.

Forsyth, R., et al., Graphene Field Effect Transistors for Biomedical Applications: Current Status and Future Prospects. Diagnostics (Basel). Jul. 26, 2017;7(3), 18 pages. pii: E45. doi: 10.3390/diagnostics7030045.

Fu, B.X., "Salt-Induced Disaggregation/Solubilization of Gliadin and Glutenin Proteins in Water," Journal of Cereal Science 24 (1996) 241-246.

Gao, N., et al., Specific detection of biomolecules in physiological solutions using graphene transistor biosensors. Proc Natl Acad Sci U S A. Dec. 20, 2016;113(51):14633-14638. doi: 10.1073/pnas. 1625010114. Epub Dec. 5, 2016.

Garcia-Aljaro, C., et al., "Carbon Nanotubes-Based Chemiresistive Biosensors for Detection of Microorganisms," Biosensors and Bioelectronics 26 (2010) 1437-1441.

Gowda, P., et al., Chemical Vapor Detection Using Nonlinear Electrical Properties of Carbon Nanotube Bundles, Nanotechnology vol. 25 (2014) pp. 1-5.

Greene, F., "In Vitro Synthesis of Wheat (*Triticum aestivum* L.) Storage Proteins1," Plant Physiol. (1981) vol. 68, pp. 778-783.

Heller, D., et al., "Peptide Secondary Structure Modulates Single-Walled Carbon Nanotube Fluorescence as a Chaperone Sensor for Nitroaromatics," PNAS May 24, 2011, vol. 108, No. 21, pp. 8544-8549.

Hnaien, M., et al., "Impedimetric Microbial Biosensor Based on Single Wall Carbon Nanotube Modified Microelectrodes for Trichloroethylene Detection," Electrochimica Acta 56 (2011) pp. 10353-10358.

Hoaglan, R., "The Determination of Gliadin or Alcohol-Soluble Protein in Wheat Flour," The Journal of Industrial and Engineering Chemistry, (1911), Proteins of The Wheat Kernel Pub by Carnegie Inst, pp. 838-842.

Huang, T.S. et al., "Immobilization of Antibodies and Bacterial Binding on Nanodiamond and Carbon Nanotubes for Biosensor Applications," Diamond and Related Materials vol. 13, (2004), pp. 1098-1102.

Huang, Y., et al., "Graphene-Based Biosensors for Detection of Bacteria and Their Metabolic Activities", Journal of Materials Chemistry, (2011) vol. 21, pp. 12358-12362.

Hui, Y., et al., "A 2.8 Ghz Combined Mode of Vibration Aluminum Nitride MEMS Resonator With High Figure of Merit Exceeding 45," (2013) Joint UFFC, EFTF and PFM Symposium pp. 930-932.

Hui, Y., et al., "Resonant Infrared Detector Based on a Piezoelectric Fishnet Metasurface," (2015) IEEE, pp. 1-3.

Huntington, M.D., et al., A Portable, Benchtop Photolithography System Based,"On a Solid-State Light Source," Small (2011), vol. 7, No. 22, pp. 3144-3147.

Huntington, M.D., et al., A Portable, Benchtop Photolithography System Based,"On a Solid-State Light Source," Supporting Information, Small, (2011), pp. S1-S7.

International Preliminary Report on Patentability for Application No. PCT/US2015/053793, mailed Apr. 13, 2017 (11 Pages).

International Search Report and Written Opinion for Application No. PCT/US2015/053793, mailed Jan. 4, 2016 (12 Pages).

International Search Report and Written Opinion for Application No. PCT/US2019/15579, mailed Jun. 18, 2019 (13 pages).

International Search Report and Written Opinion for Application No. PCT/US2019/34043, mailed Sep. 30, 2019 (12 Pages).

Jai, Fei, et al. "Impedimetric *Salmonella* aptasensor using a glassy carbon electrode modified with an electrodeposited composite consisting of reduced graphene oxide and carbon nanotubes." Microchimica Acta 183.1: 337-344. (Year: 2015).

Jain, S., et al., "Development of an Antibody Functionalized Carbon Nanotube Biosensor for Foodborne Bacterial Pathogens," J Biosens Bioelectron (2012), S:11, pp. 1-7.

Jiang, P., et al., "Molecular Mechanisms of Sweet Receptor Function," Chem. Senses 30 (Suppl 1): (2005), pp. 117-118.

Jin, X., et al., "Detection of Human Adenovirus Hexon Antigen Using Carbon Nanotube Sensors," Journal of Virological Methods vol. 171, (2011), pp. 405-407.

Kabbe, G., Presentation "Functionalization: Tailoring Nanocarbons Through Attached Molecules and Particles," Freie Universitat Berlin, (2011).

Kang, J.H., et al., An extracorporeal blood-cleansing device for sepsis therapy. Nat Med. Oct. 2014;20(10):1211-6. doi: 10.1038/nm.3640. Epub Sep. 14, 2014.

Ke, G., et al., "A Novel Strategy to Functionalize Carbon Nanotubes With Cellulose Acetate Using Triazines as Intermediated Functional Groups," Carbohydrate Polymers 79 (2010), pp. 775-782.

Kim, B., et al., "Family-Selective Detection of Antibiotics Using Antibody-Functionalized Carbon Nanotube Sensors," Sensors and Actuators B 166-167 (2012) pp. 193-199.

Huang, "Graphene-based biosensors for detection of bacteria and their metabolic activities," Journal of Materials Chemistry 21.33 (2011), 12358-12362, (Year: 2011), 5 pgs.

Nawana, Final Office Action, U.S. Appl. No. 16/422,743, Jan. 13, 2022, 15 pgs.

Nawana, Office Action, U.S. Appl. No. 16/422,743, Jun. 8, 2022, 15 pgs.

Singal, "Electroactive graphene-multi-walled carbon nanotube hybrid supported impedimetric immunosensor for the detection of human cardiac troponin-I," RSC advabces 5.92 (2015), 74994-75003, (Year: 2015), 8 pgs.

Silva, "An ultrasensitive human cardiac troponin T graphene screen-printed electrode based on electropolymerized-molecularly imprinted conducting polymer," Biosensors and Bioelectronics 77 (2016), 978-985, (Year: 2016, 8 pgs.

Zheng, "Fabrication of ultrasensitive field-effect transistor DNA biosensors by a directional transfer technique based on CVD-grown graphene," ACS applied materials & interfaces 7.31 (2015), 16953-16959, (Year: 2015), 7 pgs.

Bonanni, Allessandra et al. "Graphene for Impedimetric Biosensing", Trac Trends in Analytical Chemistry, vol. 37, 2012, pp. 12-21.

Elnathan, Roey, et al. "Biorecognition layer engineering: overcoming screening limitations of nanowire-based FET devices." Nano letters 12.10 (2012): 5245-5254. (Year: 2012).

European Examination Report, EP19215320.3, dated Feb. 16, 2023, 6 pages.

European Office Action for Application No. 15846637.5, dated May 10, 2019 (6 pages).

European Search Report for U.S. Appl. No. 19/215,320, dated Aug. 13, 2020 (9 pages).

Google Machine Translation of WO-2017194746-A1, (https://patents.google.com/patent/WO2017194746A1/en?oq=pct%2fep2017%2f061479) p. 1-15. (Year: 2017).

(56) References Cited

OTHER PUBLICATIONS

Gutes, Albert et al. "Impedimetric Graphene-based Biosensors for the Detection of Polybrominated Diphenyl Ethers", Nanoscale, vol. 5, No. 13, Jan. 1, 2013, pp. 6048.
Huang, Yinxi, et al. "Graphene-based biosensors for detection of bacteria and their metabolic activities." Journal of Materials Chemistry 21.33 (2011): 12358-12362.
Interantional Search Report and Written Opinion for Application No. PCT/US2020/027827, dated Aug. 17, 2020 (14 Pages).
Kumeria, Tushar, et al. "Label-free reflectometric interference microchip biosensor based on nanoporous alumina for detection of circulating tumour cells." Biosensors and Bioelectronics 35.1 (2012): 167-173. (Year: 2012).
Labroo, Pratima, and Yue Cui. "Graphene nano-ink biosensor arrays on a microfluidic paper for multiplexed detection of metabolites." Analytica Chimica Acta 813 (2014): 90-96. (Year: 2014).
Machine Translation: DE 19600521 A1, Google Patents, p. 1-5.
Maehashi, Kenzo, and Kazuhiko Matsumoto. "Label-free electrical detection using carbon nanotube-based biosensors." Sensors 9. 7 (2009): 5368-5378. (Year: 2009).
Nehra, Anuj, and Krishna Pal Singh. "Current trends in nanomaterial embedded field effect transistor-based biosensor." Biosensors and Bioelectronics 74 (2015): 731-743. (Year: 2015).
Neves et al. An electrochemical deamidated gliadin antibody immunosensor for celiac disease clinical diagnosis. Analyst. Apr. 7, 2013;138(7):1956-8. doi: 10.1039/c3an36728b. Epub Feb. 12, 2013.
Pena-Bahamonde, Janire, et al. "Recent Advances in Graphene-Based Biosensor Technnology with Applications in Life Sciences", J. Nanobiotechnol, Jan. 1, 2018, pp. 75.
Saurabh, S., et al., "Graphene Oxide-Based Biosensor for Food Toxin Detection", Applied Biochemistry and Biotechnology, Humana Press, Inc. New York, vol. 17, No. 3, Jun. 11, 2014.
Shao, Ning, Eric Wickstrom, and Balaji Panchapakesan. "Nanotube-antibody biosensor arrays for the detection of circulating breast cancer cells." Nanotechnology 19.46 (2008): 465101. (Year: 2008).
Zheng et al., "Fabrication of Ultrasensitive FieldEffect Transistor DNA Biosensors by a Directional Transfer Technique Based on CVDGrown Graphene", ACS Applied Materials & Interfaces 2015 7 (31), pp. 16953-16959.
Thakur et al., "Rapid detection of single *E. coli* bacteria using a graphene-based field-effect transistor device, Biosensors and Bioelectronics", vol. 110, 2018, pp. 16-22.
Than, et al. "Graphene Field-Effect Transistor and Its Application for Electronic Sensing" Small; 2014; vol. 10; No. 20; pp. 4042-4065.
Tuteja et al., "Graphene-gated biochip for the detection of cardiac marker Troponin I". Anal Chim Acta. Jan. 27, 2014;809: pp. 148-154.
U.S. Appl. No. 17/027,029, filed Sep. 21, 2020, Device and Method for Chemical Analysis.
U.S. Appl. No. 16/422,743, filed May 24, 2019, Functionalized Sensor for Detection of Biomarkers.
U.S. Appl. No. 17/152,513, filed Jan. 19, 2021, Point-of-Collection Graphene-Based Toxicology Sensor.
U.S. Appl. No. 17/170,439, filed Feb. 8, 2021, Graphene-Based Sensor for Detecting Hemoglobin in a Biological Sample.
U.S. Appl. No. 17/208,692, filed Mar. 22, 2021, Graphene-Based Sensor for Detecting Sars-Cov-2 Virus in a Biological Sample.
U.S. Appl. No. 17/542,402, filed Dec. 4, 2021, Devices and Methods for Detecting Analytes Using Functionalized Carbon Allotropes.
U.S. Appl. No. 17/542,400, filed Dec. 4, 2021, Graphene-Based Sensor for Detection of Prostate Biomarkers.
U.S. Appl. No. 17/751,364, filed May 23, 2022, Device for Collection of Biological Samples.
U.S. Appl. No. 17/969,614, filed Oct. 19, 2022, Graphene-Functionalized Sensor Surfaces and Related Methods.
U.S. Appl. No. 18/071,887, filed Nov. 30, 2022, Systems and Methods for Processing and Testing Biological Samples.
U.S. Appl. No. 18/072,106, filed Nov. 30, 2022, System and Method for Testing Biological Samples.
U.S. Appl. No. 14/874,228, filed Oct. 2, 2015, Device and Method for Chemical Analysis.
U.S. Appl. No. 15/357,445, filed Nov. 21, 2016, Device and Method for Chemical Analysis.
U.S. Appl. No. 16/422,770, filed May 24, 2019, Device and Method for Chemical Analysis.
U.S. Appl. No. 16/046,675, filed Jul. 26, 2018, Device and Method for Chemical Analysis.
U.S. Appl. No. 16/260,773, filed Jan. 29, 2019, Methods and Devices for Detection of Pathogens.
Alessandra et al., "Graphene for impedimetric biosensing", TRAC Trends in Analytical Chemistry, vol. 37, 2012, pp. 12-21, XP028398672.
Ali et al., "Microfluidic immuno-biochip for detection of breast cancer biomarkers using hierarchical composite of porous graphene and titanium dioxide nanofibers." ACS Applied Materials & Interfaces, 2016, p. 20570-20582.
Australian Examination Report for Australian Application No. 2019211495 dated Nov. 30, 2023.
Bhavsar et al., "A cytokine immunosensor for Multiple Sclerosis detection based upon label-free electrochemical impedance spectroscopy using electroplated printed circuit board electrodes.", Biosensors and Bioelectronics, 2009, p. 506-509.
European Search Report for European patent application No. 20720731.7 dated Nov. 24, 2023.
Japanese Office Action for Japanese Application No. 2021-560720 dated Dec. 21, 2023 (includes English language translation).
Kim, Jun Pyo, et al. "Ultrasensitive carbon nanotube-based biosensors using antibody-binding fragments." Analytical biochemistry 381.2 (2008): 193-198. (Year: 2008).
Tsai, et al., "Direct correlation between potentiometric and impedance biosensing of antibody-antigen interactions using an integrated system.", Applied Physics Letters, 2017.

\* cited by examiner

METHODS AND DEVICES FOR DETECTION OF THC

CROSS-REFERENCE TO RELATED APPLICATIONS

The present disclosure claims priority to U.S. Provisional Application No. 62/832,264, filed Apr. 10, 2019 and titled "Methods and Devices for Detection of THC." The present disclosure is also a continuation-in-part of U.S. application Ser. No. 16/422,743, filed May 24, 2019 and titled "A Functionalized Sensor for Detection of Biomarkers." U.S. application Ser. No. 16/422,743 claims priority to U.S. Provisional Application No. 62/676,079, filed May 24, 2018 and titled "Graphene-Functionalized Sensor." The entire contents of each of these applications are incorporated herein by reference.

FIELD

The present invention relates generally to methods and devices for the detection of tetrahydrocannabinol (THC) and cannabidiol (CBD).

BACKGROUND

*Cannabis*, which is also known as marijuana, is a psychoactive drug from the *Cannabis* plant. It is used increasingly for medical and recreational purposes. The main psychoactive component of *cannabis* is tetrahydrocannabinol (THC).

With the increase use of *cannabis*, including in food products, methods and systems are needed for easy detection of THC in a variety of different products.

SUMMARY

In one aspect, a method of detecting tetrahydrocannabinol (THC) in a sample is disclosed, which comprises bringing the sample into contact with a graphene layer functionalized with an antibody exhibiting specific binding to THC, applying a time-varying electric field to said antibody-functionalized graphene layer, monitoring at least one electrical property, e.g., electrical resistance, of said graphene layer in response to interaction with said sample, and detecting presence of THC in the sample by detecting a change in said electrical resistance indicative of interaction of THC with said anti-body functionalized graphene layer.

In some embodiments, the time-varying electric field has a frequency in a range of about 1 kHz to about 2 MHz, e.g., in a range of 100 kHz to about 1 MHz, such as 500 kHz.

In some embodiments, the graphene layer can be disposed on an underlying substrate. A variety of substrates can be employed. Some suitable examples include, without limitation, a semiconductor substrate and glass.

The graphene layer can be electrically coupled to a pair of electrically conductive pads for facilitating the measurement of the electrical conductivity of the antibody-functionalized graphene layer, and specifically, the measurement of a change, if any, in the electrical conductivity of the antibody-functionalized graphene layer in response to interaction with a sample under study.

The methods and systems according to the present teachings can be employed to detect the presence of THC in a variety of different samples, including, food samples, medications, biological samples, such as blood, urine and saliva.

In some embodiments, the method is employed to detect Δ-9-THC. In some embodiments, the method is employed to detect one or more metabolites of Δ-9-THC, such as 11-OH-THC and 11-COOH-THC. In some embodiments, the method can be employed for concurrent detection of Δ-9-THC and any, or both, of 11-OH-THC and 11-COOH-THC.

In some embodiments, the method can exhibit a limit-of-detection of better than 20 ng/ml to 100 ng/ml.

In a related aspect, a system for detecting THC in a sample is disclosed, which comprises a sensor having a substrate, and a graphene layer deposited on a surface of said substrate, said graphene layer being functionalized with a plurality of antibodies exhibiting specific binding to THC. The sensor can further include at least a pair of electrically conductive pads coupled to the graphene layer for measuring an electrical property, e.g., an electrical resistance, thereof. A reference electrode can be disposed on the substrate in proximity of the antibody-functionalized graphene layer to allow application of a reference AC voltage thereto, via an AC voltage source. In some embodiments, such a reference electrode can be positioned above the graphene layer. In some embodiments, the distance between the reference electrode and the antibody-functionalized graphene layer can be, for example, in a range of 100 microns to about 3 mm, e.g., about 1 to about 2 mm.

The applied AC voltage can have a frequency in a range of about 1 kHz to about 2 MHz, e.g., 1 MHz, and an amplitude in a range of about 1 millivolt to about 3 volts. In some embodiments, in addition to the AC voltage, a ramp voltage (e.g., in a range of about −10 V to about 10 V, e.g., about −1 V to 1 V) can applied to the reference electrode during data acquisition. In other words, a dc offset of the AC voltage is ramped, e.g., in a range of about −10 V to about 10 V, e.g., in a range of about −1 V to about 1 V.

In some embodiments, THC includes Δ-9-THC. In some embodiments, THC includes a hydroxylated, or carboxylated metabolite of Δ-9-THC. Some examples of such metabolites include, without limitation, 11-COOH-THC. In some embodiments, THC includes 11-COOH-THC. In some embodiments, the sensor is configured to detect Δ-9-THC as well as one or more metabolites of 11-OH-THC and 11-COOH-THC. In some embodiments, THC includes Δ-8-THC and/or one of its metabolites.

In a related aspect, a method of detecting cannabidiol (CBD) in a sample is disclosed, which includes bringing the sample into contact with a graphene layer functionalized with an antibody exhibiting specific binding to CBD, applying a time-varying electric field to said antibody-functionalized graphene layer, monitoring at least one electrical property of the graphene layer in response to interaction with said sample, and detecting presence of CBD in the sample by detecting a change in said electrical property indicative of interaction of CBD with the anti-body functionalized graphene layer.

In a related aspect, a system for detecting CBD in a sample is disclosed, which includes a sensor, comprising a substrate and a graphene layer deposited on a surface of said substrate, said graphene layer being functionalized with a plurality of antibodies exhibiting specific binding to CBD, and at least one pair of electrically conductive pads coupled to said graphene layer for measuring an electrical property of the antibody-functionalized graphene layer in response to exposure thereof to a sample under study. In some embodiments, the measured electrical property of the antibody-functionalized graphene layer can be its electrical resistance, e.g., its DC electrical resistance.

Further understanding of various aspects of the invention can be obtained by reference to the following detailed description in conjunction with the associated drawings, which are briefly described below.

DETAILED DESCRIPTION

It has been discovered that the change in the conductivity of an antibody-functionalized graphene layer can be employed to detect the presence of tetrahydrocannabinol (THC) in a sample. The present teachings are generally related to graphene-based sensors that can be employed for detection of THC in a sample, including metabolites of *cannabis* consumption.

An "antibody," as that term is used herein, refers to a polypeptide that exhibit specific binding affinity, e.g., an immunoglobulin chain or fragment thereof, comprising at least one functional immunoglobulin variable domain sequence. An antibody encompasses full length antibodies and antibody fragments. In some embodiments, an antibody comprises an antigen binding or functional fragment of a full-length antibody, or a full-length immunoglobulin chain. For example, a full-length antibody is an immunoglobulin (Ig) molecule (e.g., an IgG antibody) that is naturally occurring or formed by normal immunoglobulin gene fragment recombinatorial processes. In embodiments, an antibody refers to an immunologically active, antigen-binding portion of an immunoglobulin molecule, such as an antibody fragment. An antibody fragment, e.g., functional fragment, comprises a portion of an antibody, e.g., Fab, Fab', F(ab')2, F(ab)2, variable fragment (Fv), domain antibody (dAb), or single chain variable fragment (scFv). A functional antibody fragment binds to the same antigen as that recognized by the intact (e.g., full-length) antibody.

The term "antibody" also encompasses whole or antigen binding fragments of domain, or signal domain, antibodies, which can also be referred to as "sdAb" or "VHH." Domain antibodies comprise either $V_H$ or $V_L$ that can act as stand-alone, antibody fragments. Additionally, domain antibodies include heavy-chain-only antibodies (HCAbs). Antibody molecules can be monospecific (e.g., monovalent or bivalent), bispecific (e.g., bivalent, trivalent, tetravalent, pentavalent, or hexavalent), trispecific (e.g., trivalent, tetravalent, pentavalent, hexavalent), or with higher orders of specificity (e.g., tetraspecific) and/or higher orders of valency beyond hexavalency. An antibody molecule can comprise a functional fragment of a light chain variable region and a functional fragment of a heavy chain variable region, or heavy and light chains may be fused together into a single polypeptide.

The term "immunogen" as used herein refers to a substance that is capable of inducing a humoral antibody response.

Various terms are used herein in accordance with their ordinary meanings in the art. The term "about" as used herein to modify a numerical value is intended to denote a variation of at most 10% of a numerical value.

Figure 1:
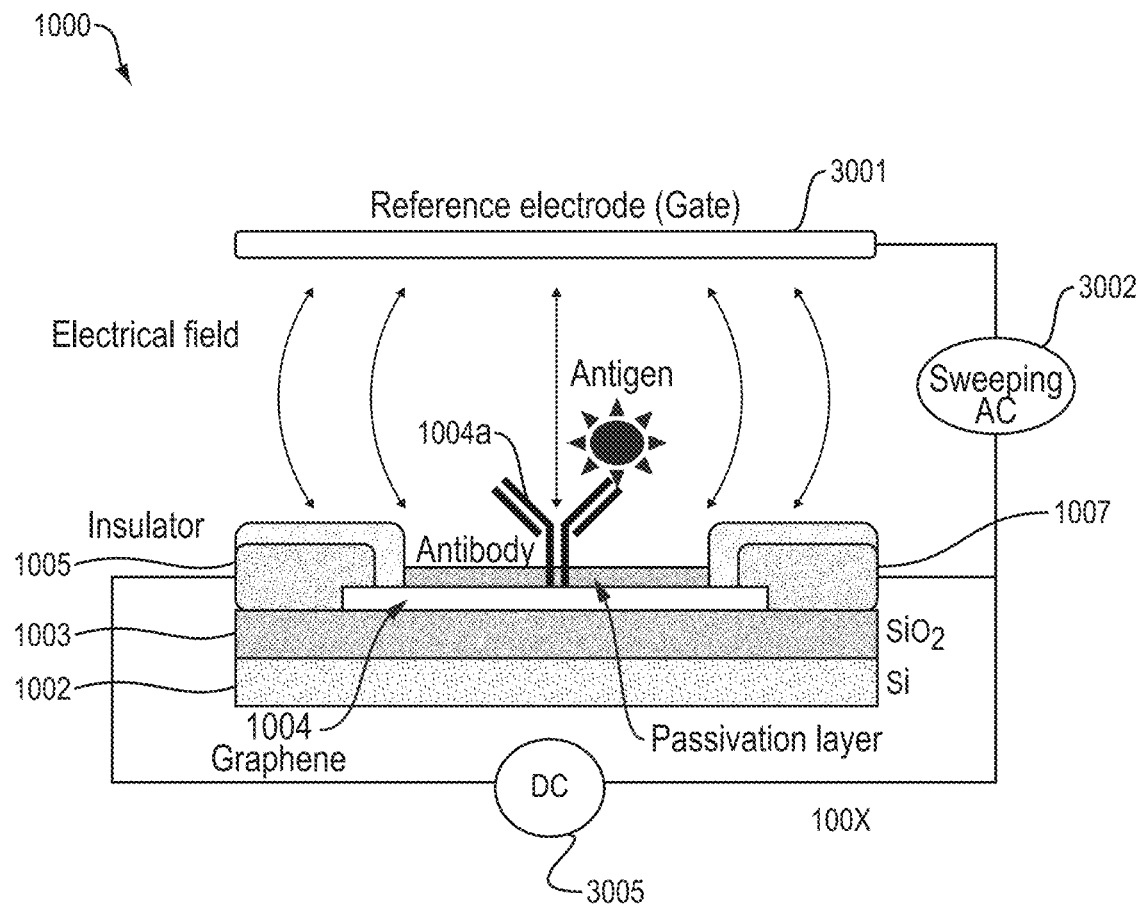
FIG. 1 schematically depicts a sensor system according to an embodiment of the present teachings for detecting THC in a sample.
Figure 2:
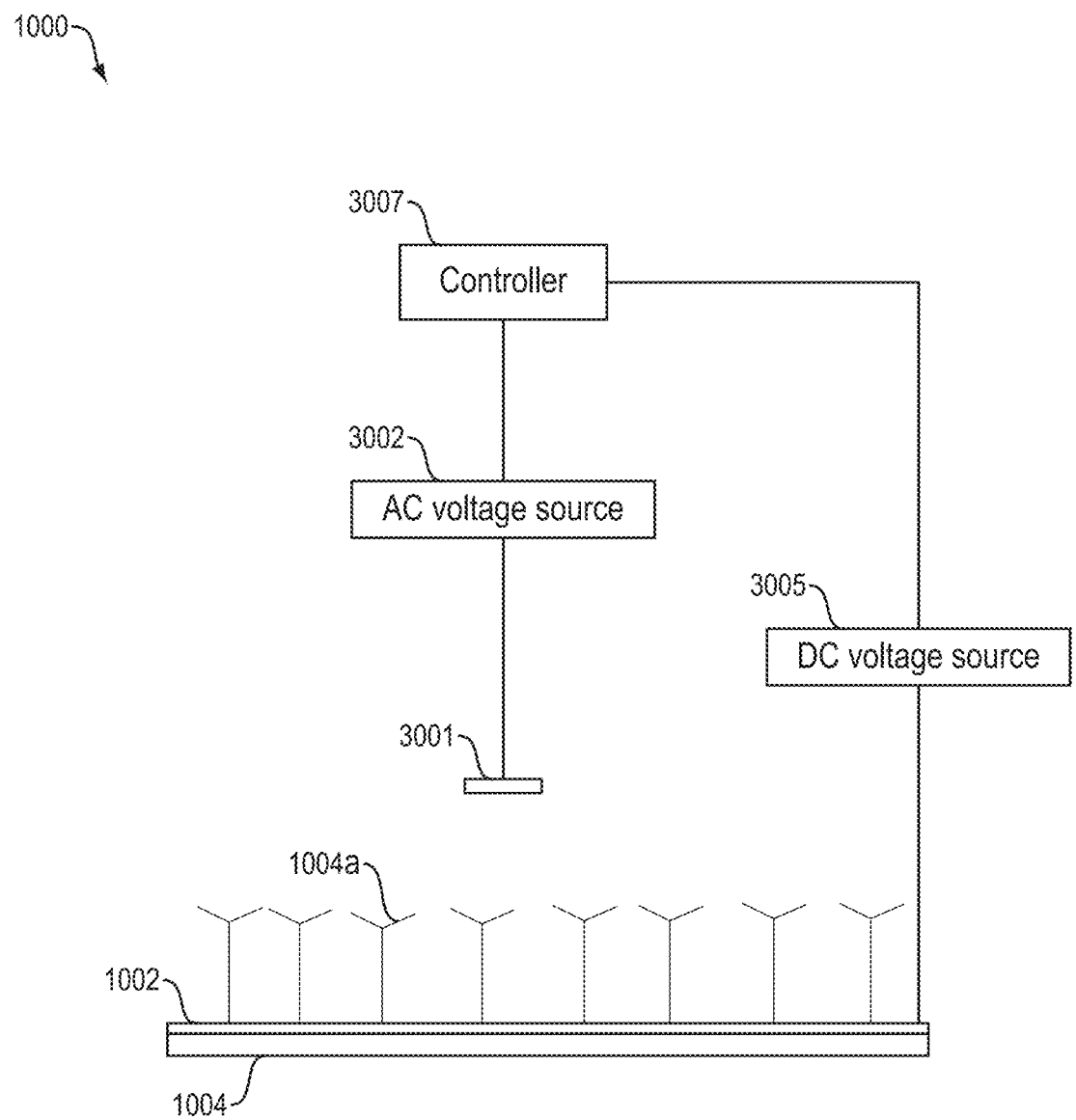
FIG. 2 is another schematic view of the sensor depicted in FIG. 1 as well as an AC and DC source for applying AC and/or DC voltage/current to the antibody-functionalized graphene layer and a controller for controlling the AC and DC source.

FIGS. 1 and 2 schematically depict an example of a device 1000 (herein also referred to as sensor 1000) according to an embodiment of the present teachings for detecting THC in a sample. The device 1000 includes a substrate 1002 on a top surface of which a layer of graphene 1004 is deposited. A variety of different substrates can be employed. By way of example, the substrate 1002 can be any of a semiconductor, such as silicon, glass, or plastic. In this embodiment, a silicon oxide layer 1003 separates the underlying silicon layer from the graphene layer.

In this embodiment, the graphene layer is functionalized with an antibody 1004a that can specifically bind to THC. By way of example, in some embodiments, the graphene layer can be functionalized with a commercially available antibody, such as an antibody marketed by Fitzgerald Industries (#10-T43B). Two metallic pads 1005/1007 in electrical contact with the graphene layer allow measuring the electrical resistance of the antibody-functionalized graphene layer, and particularly, a change in the electrical resistance of the graphene layer in response to exposure thereof to a sample containing THC. In some embodiments, the electrically conductive pads can be formed of silver high conductive paste, though other electrically conductive materials can also be employed. The conductive pads can be electrically connected to a measurement device, e.g., a voltmeter, via a plurality of conductive wires for measuring the Ohmic electrical resistance of the graphene layer.

In this embodiment, the sensor 1000 includes a reference electrode 3001 disposed in proximity of the antibody-functionalized graphene layer, e.g., at a distance in a range of about 50 micrometers to about a few millimeters (e.g., 1-2 millimeters) on the silicon oxide layer 1003, or alternatively, above the functionalized graphene layer. The reference electrode can be utilized to generate a time-varying electric field at the interface of the functionalized graphene layer and the sample in contact with that layer. For example, in this embodiment, an AC voltage source 3002 can be employed to apply an AC voltage to the reference electrode, which can in turn result in the generation of a time-varying electric field in the space between the reference electrode and the functionalized graphene layer. As discussed in more detail below, the AC voltage source 3002 can also apply a DC offset voltage to the reference electrode. In other embodiments, a sensor according to the present teachings may not include a reference electrode.

Further, a power supply 3005 is provided for applying a DC voltage across, or a DC current to, the antibody-functionalized graphene layer to measure a response thereof (e.g., a change in a voltage across the antibody-functionalized layer when a constant current is applied to that layer) upon exposure of the antibody-functionalized layer to a sample under study.

More specifically, a controller 3007 (see FIG. 2) is programmed to control the AC and the DC sources. Although in this embodiment the AC voltage source 3002 and the power supply 3005 are shown as two independent units, in other embodiments the functionalities of the AC voltage source for applying an AC voltage and a DC offset voltage to the reference electrode and that of the power supply 3003 can be combined in a single unit.

The controller 3007 can be implemented in hardware, software, and/or firmware in a manner known in the art as informed by the present teachings. For example, the controller 3007 can have the components illustrated in FIG. 6 for the analyzer.

In other embodiments, a sensor according to the present teachings can be implemented without the reference AC electrode.

Figure 3:
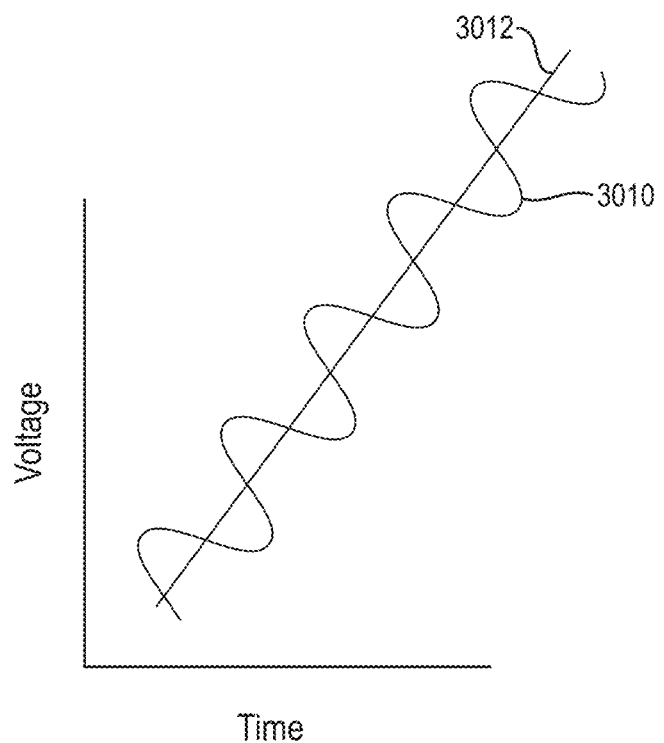
FIG. 3 schematically depicts a combination of a ramp voltage and an AC voltage applied to the reference electrode of the sensor shown in FIG. 1.

By way of illustration, FIG. 3 schematically depicts a combination of an AC voltage 3010 and a DC offset voltage 3012 applied to the reference electrode. By way of example, the DC offset voltage can extend from about −10 V to about 10 V (e.g., from −1 V to about 1 V), and the applied AC voltage can have the frequencies and amplitudes disclosed above.

Without being limited to any particular theory, in some embodiments, it is expected that the application of such an AC voltage to the reference electrode can minimize, and preferably eliminate, an effective capacitance associated with a sample, e.g., a liquid sample, with which the functionalized graphene layer is brought into contact as the sample is being tested, thereby facilitating the detection of a change in the resistance of the underlying graphene layer in response to the interaction of the antibodies with THC present in the sample. In some cases, the effective capacitance of the sample can be due to ions present in the sample.

The application of a such a time-varying electric field to the interface between the graphene layer and the liquid in contact with the graphene layer can advantageously facilitate the detection of one or more electrical properties of the antibody-functionalized graphene layer, e.g., a change in its resistance in response to its interaction with a THC present in a sample under investigation. In particular, it has been discovered that the application of an AC voltage having a frequency in a range of about 1 kHz to about 2 MHz, e.g., in a range of about 100 kHz to about 1 MHz, or 10 kHz to about 500 kHz or in a range of about 20 kHz to about 400 kHz, or in a range of about 30 kHz to about 300 kHz, or in a range of about 40 kHz to about 200 kHz, can be especially advantageous in this regard. By way of example, the amplitude of the AC voltage applied to the reference electrode can be in a range of about 1 millivolt to about 3 volts, e.g., in a range of about 100 millivolts to about 2 volts, or in range of about 200 millivolts to about 1 volt, or in range of about 300 millivolts to about 1 volt, e.g., in a range of about 0.5 volts to 1 volt. Further, in some cases, the voltage applied to the reference electrode can have an AC component and a DC offset, where the DC offset can be in a range of about −40 volts to about +40 volts, e.g., −1 volt to about +1 volt.

In some embodiments, in use, a sample suspected of containing THC can be introduced onto the sensor 1000. Without being limited to any particular theory, the interaction of THC in the sample, if any, with the antibodies that are coupled to the underlying graphene layer can cause a change in the electrical conductivity of the graphene layer. This change in the electrical conductivity of the graphene layer can be in turn measured to detect the presence of THC in the sample under study.

Figure 4:
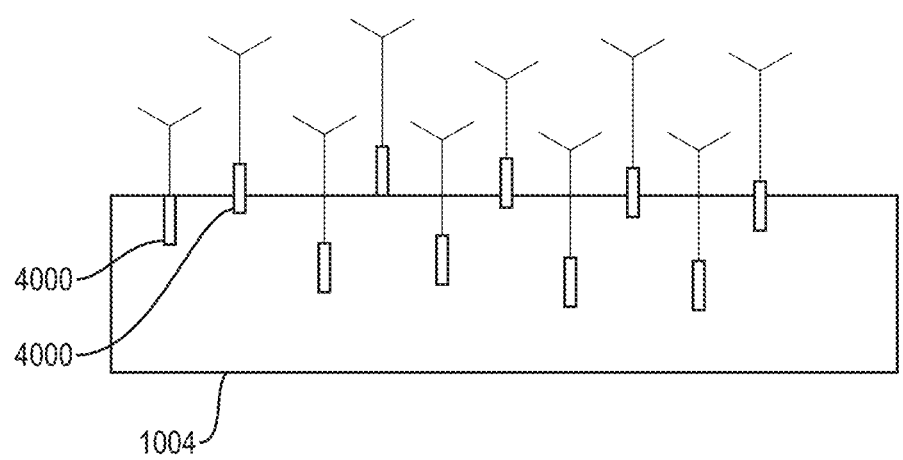
FIG. 4 schematically depicts the coupling of a plurality of antibodies to the graphene layer via a plurality of linker molecules.

In some embodiments, a linker can be employed to couple the antibodies to the graphene layer. For example, in such embodiments, a plurality of linker molecules can be bound to the graphene layer, e.g., via π-π interactions, and the antibody molecules can be in turn covalently coupled to the linker molecules. By way of example, as shown schematically in FIG. 4, a variety of linker molecules 4000 can be employed for coupling the antibodies to the underlying graphene layer 1004. By way of example, in some embodiments, 1-pyrenebutonic acid succinimidyl ester is employed as a linker to facilitate the coupling of the antibodies to the underlying graphene layer.

Figure 6:
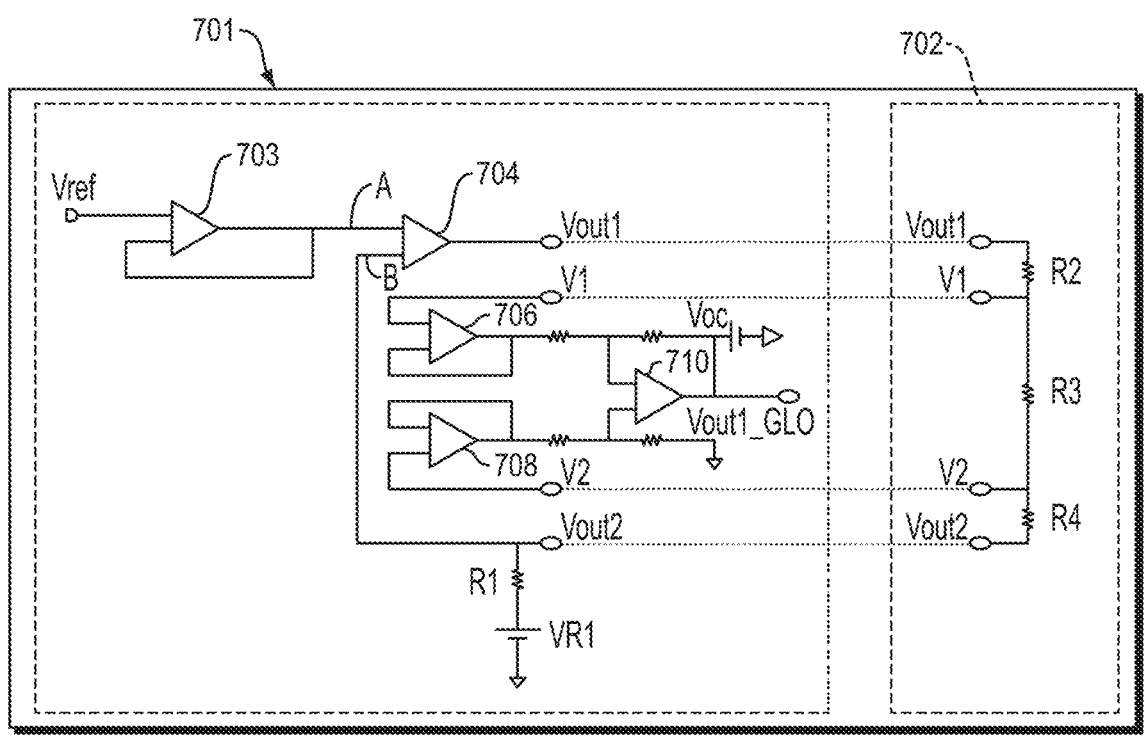
FIG. 6 schematically depicts a voltage-measuring device that can be employed in some embodiments for measuring the electrical resistance of the underlying graphene layer of a sensor according to the present teachings.

With reference to FIG. 6, in some embodiments, a voltage-measuring device 701 can be employed to measure the resistance of the underlying graphene layer. In this embodiment, such a voltage-measuring device 701 can be electrically coupled to the antibody-functionalized graphene layer via the electrical pads 1005/1007, shown in FIG. 1. The voltage-measuring module can be implemented using routine methods in the art. Specifically, FIG. 6 illustrates a sensor 702 according to the present invention as an equivalent circuit corresponding to an antibody-functionalized graphene layer. A fixed voltage V (e.g., 1.2 V) is generated at the output of a buffer operational amplifier 703. This voltage is applied to one input (A) of a downstream operational amplifier 704 whose other input B is coupled to VRI ground via a resistor R1. The output of the operational amplifier 704 (Vout1) is coupled to the other end of the sensor 702 (in this schematic diagram, resistor R2 denotes the resistance between two electrode pads at one end of the equivalent sensor 702, resistor R3 denotes the resistance of the graphene layer extending between two inner electrodes of the sensor, and resistor R4 denotes the resistance between two electrode pads at the other end of the sensor). As the operational amplifier maintains the voltage at the end of the resistor R1 that is not connected to VR1 ground at the fixed voltage applied to its input (A), e.g., 1.2 V, a constant current source is generated that provides a constant current flow through the sensor 702 and returns to ground via the resistor R1 and VR1.

The voltage generated across the antibody-functionalized graphene layer is measured via the two inner electrodes of the sensor. Specifically, one pair of the inner electrode pads is coupled to a buffer operational amplifier 706 and the other pair is coupled to the other buffer operational amplifier 708. The outputs of the buffer operational amplifiers are applied to the input ports of a differential amplifier 710 whose output port provides the voltage difference across the antibody-functionalized graphene layer. This voltage difference ($V_{out1}$–GLO) can then be used to measure the resistance exhibited by the antibody-functionalized graphene layer. The current forced through R3 is set by I=(Vref−VR1)/R1, where the value of VR1 is digitally controlled. For each value of current I, the corresponding voltage (Vout1_GLO) is measured and stored. The resistance of the antibody-functionalized graphene layer can be calculated as the derivative of the voltage, Vout1_GLO, with respect to current I, i.e., R=dV/dI.

Figure 7:
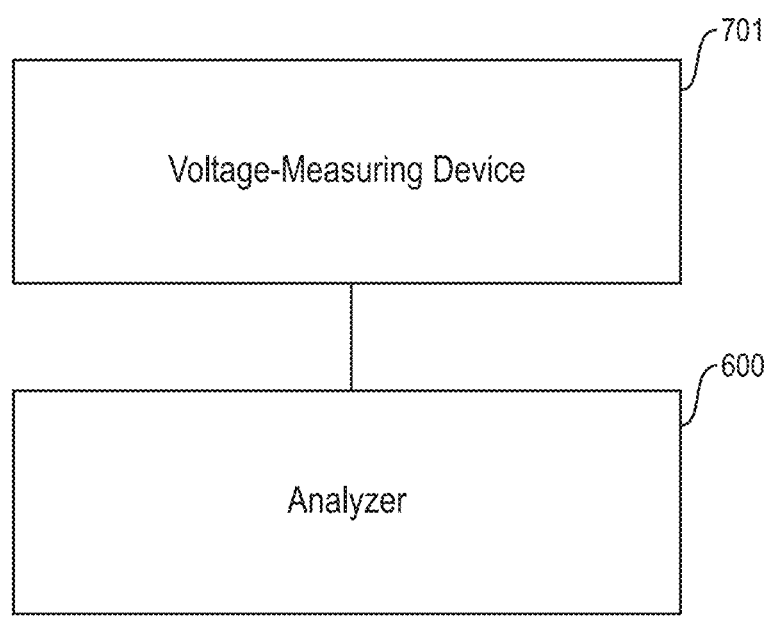
FIG. 7 schematically depicts an analyzer in communication with the voltage-measuring device depicted in FIG. 6.

As shown schematically in FIG. 7, in some embodiments, an analyzer 600 can be in communication with the voltage measuring circuitry 701 to receive the applied current and the measured voltage value and use these values to calculate the resistance of the antibody-functionalized graphene layer. The analyzer can then employ the calculated resistance, e.g., a change in the resistance in response to exposure of the antibody-functionalized graphene layer to a sample under investigation, to determine, in accordance with the present teachings, whether the sample contains an immunogen of interest.

Figure 8:
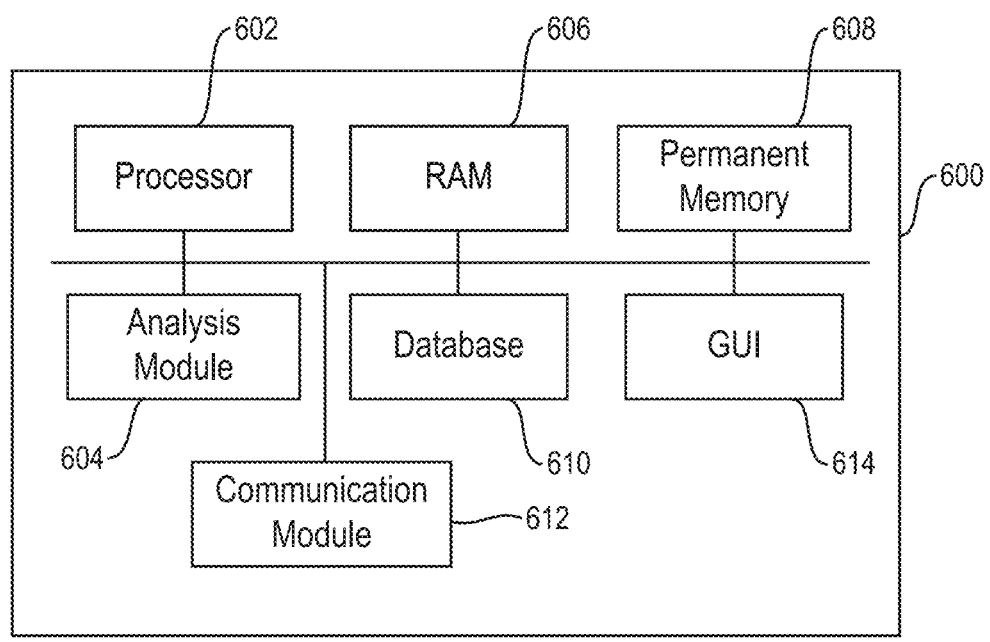
FIG. 8 schematically depicts an example of implementation of the analyzer depicted in FIG. 7.

By way of example, as shown schematically in FIG. 8, in this embodiment, the analyzer 600 can include a processor 602, an analysis module 604, a random access memory (RAM) 606, a permanent memory 608, a database 610, a communication module 612, and a graphical user interface (GUI) 614. The analyzer 600 can employ the communication module 612 to communicate with the voltage measuring circuitry 701 to receive the values of the applied current and the measured voltage. The communication module 612 can be a wired or a wireless communication module. The analyzer 600 further includes a graphical user interface (GUI) 614 that allows a user to interact with the analyzer 600.

The analysis module 604 can employ the values of a current applied to the antibody-functionalized graphene layer as well as the voltage induced across the graphene layer to calculate a change in the resistance of the antibody-functionalized graphene layer in response to exposure thereof to a sample under investigation. The instructions for such calculation can be stored in the permanent memory 608 and can be transferred at runtime to RAM 606 via processor 602 for use by the analysis module 604. In some embodiments, the database 610 can store calibration data that can be employed for determining whether a pathogen of interest is present in a sample under study. By way of example, the database 610 can store calibration data indicative of a temporal change in the electrical resistance of an antibody-functionalized graphene layer in response to exposure to a particular pathogen. A comparison of a measured temporal variation of a similar antibody-functionalized graphene exposed to a sample suspected of containing the pathogen with the calibrated response can be used to determine whether the pathogen is present in the sample. The GUI 614 can allow a user to interact with the analyzer 600.

By way of example, a suitable voltage-measuring module is disclosed in U.S. Pat. No. 9,664,674, which is herein incorporated by reference in its entirety.

In another embodiment, a constant DC voltage can be applied across the functionalized graphene layer via a DC voltage source and a change in the current flowing through the functionalized graphene layer can be measured to determine whether THC is present in a sample under test. The DC voltage source and the circuitry for measuring the current can be implemented using known methods as informed by the present teachings.

Figure 5A:
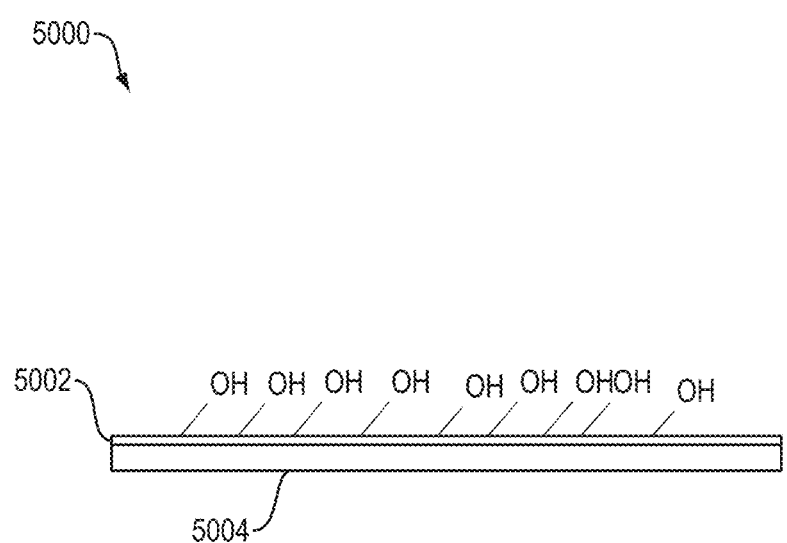
FIG. 5A schematically depicts a hydroxyl-functionalized graphene layer.
Figure 5B:
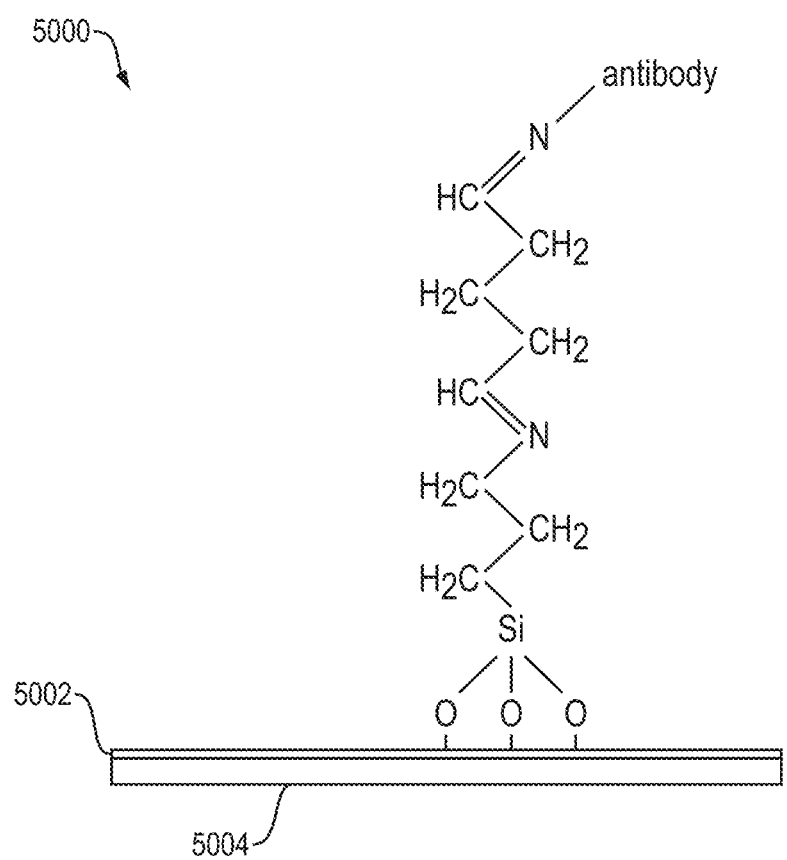
FIG. 5B schematically depicts a hydroxyl-functionalized graphene layer to which antibodies are attached.

With reference to FIGS. 5A and 5B, in some embodiments, a sensor 5000 according to the present teachings can include a hydroxyl-functionalized graphene layer 5002 that is further functionalized with anti-THC antibodies via a molecule containing an aldehyde moiety.

More specifically, with reference to FIG. 5B, in this embodiment, the hydroxyl-functionalized graphene layer 5002 can be incubated with 2% 3-Aminopropyl triethoxysilane (APTES) in 95% ethanol for 1 hour to allow for aqueous silanization of the surface. The graphene layer can then be incubated in 2.5% glutaraldehyde in milli-Q water for a few hours (e.g., for 2 hours). This incubation can create aldehyde groups (—COH), which can react with amine groups (—NH$_2$) of the antibody, e.g., via a covalent bond, thus coupling the antibody to the hydroxyl-functionalized graphene layer.

Similar to the previous embodiment, in this embodiment, the graphene layer can be initially deposited on an underlying substrate 5004. The underlying substrate 5004 can be, for example, a semiconductor, such as silicon, or a polymeric substrate, e.g., plastic.

Though not shown in FIG. 5B, similar to the above sensor 1000, the sensor 5000 includes metallic pads that can allow application of an electrical signal (e.g., a current or a voltage) to the antibody-functionalized graphene layer and monitor at least one electrical property of the antibody-functionalized graphene layer, e.g., its DC electrical resistance.

In some embodiments, a sensor according to the present teachings can be employed by law enforcement officials as an on-site testing device against illicit use of *cannabis*. In particular, in some such embodiments, a sensor according to the present teachings can detect not only Δ-9-THC but also one or more of its metabolites.

By way of example, with reference to FIG. 1, in some embodiments, the graphene layer 1004 can be functionalized with an antibody that exhibits binding not only to Δ-9-THC, or Δ-8-THC but also to one or more of its metabolites, such as hydroxylated and/or carboxylated metabolites. By way of example, a monoclonal antibody marketed by MybioSource of San Diego, CA under catalogue number MBS310888 can be used. The specification of this antibody indicates that it recognizes THC and its metabolites and does not cross-react with Opiates, Cocaine Metabolite, Amphetamines and Phencyclidine. Table 1 below provides examples of other antibodies that can be employed in the practice of the present teachings for detecting THC, e.g., Δ-9-THC, or Δ-8-THC and their metabolites.

TABLE 1

| Source | Catalogue # |
|---|---|
| Abbexa (Cedarlane) | ABX021068-1MG |
| Abbexa (Cedarlane) | ABX023622-1MG |
| Abbexa (Cedarlane) | ABX120099-1MG |
| Abbexa (Cedarlane) | ABX021066-1MG |
| Abbexa (Cedarlane) | ABX021067-1MG |

It is noted that the antibody under the catalogue number ABX021068-1MG recognizes 8-THC-BSA. Thus, in some embodiment in which the detection of 8-THC-BSA is desired, a sample under study is initially processed so as to conjugate 8-THC to BSA (bovine serum albumin) and then introduced into a sensor according to the present teachings.

In some embodiments, a blood or a urine, or a *salvia* sample can be introduced into a sensor according to the present teachings for the detection of Δ-9-THC and its metabolites. By way of example, a saliva sample can be obtained using a swab, or any other suitable device for collecting saliva from an individual, and can be subsequently placed in a suitable liquid, such as a phosphate buffer solution, to prepare a sample for testing by a sensor according to the present teachings.

In some embodiments, a sensor according to the present teachings can exhibit a limit of detection of about 20-100 ng/ml.

The two primary metabolic products of Δ-9-THC include psychoactive metabolite 11-OH-THC and non-psychoactive metabolite 11-COOH-THC. First-pass metabolism (in the liver or Phase I metabolism) also generates to a lesser degree 8β-OH-THC (epoxy-hexahydrocannabinol) and 8α-OH-THC (8-keto-THC) as part of the process. The liver (cytochrome P450 enzymes) breaks down Δ-9-THC into these hydroxylated and carboxylated metabolites:

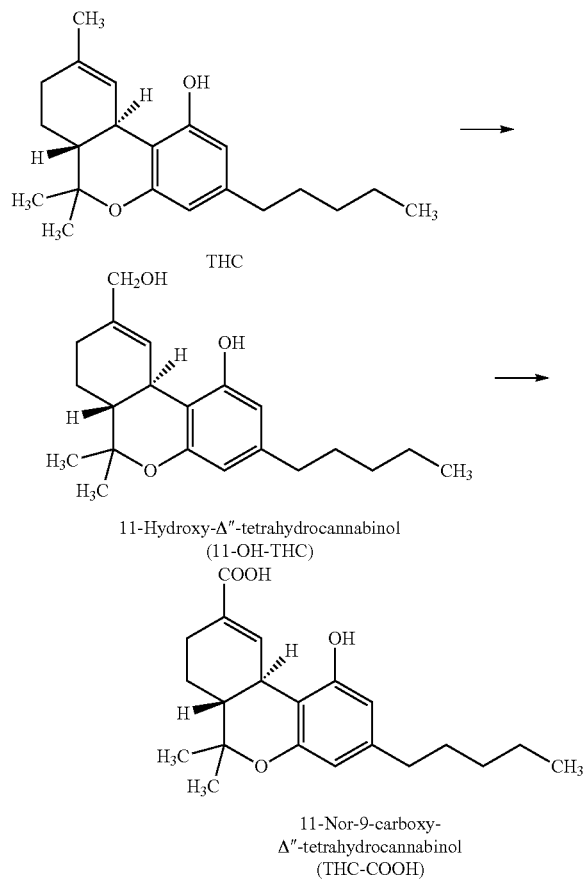

When *cannabis* is smoked, there is typically a steep increase of Δ-9-THC in the circulating blood after about 10 minutes of consumption while the blood concentration of 11-OH-THC peaks slightly later, at about 15 minutes after consumption. Subsequently, the levels of both Δ-9-THC and 11-OH-THC drop sharply between 20-30 mins and their concentrations typically fall below 0.5 ng/ml (limit of detection) after 1 hr. The blood (plasma) concentration of the non-psychoactive metabolite THC-COOH peaks later between 45-60 min after consumption and circulates in the blood stream for much longer (e.g., on average 7 days, but can be up to 12 days in chronic users), before falling below the detection limits.

The bioavailability of inhaled Δ-9-THC is typically in a range of about 10-35%, (actually can be as much as 2-56% due to variability in subject smoking dynamics), but can vary significantly among different individuals. For example, regular users can exhibit a bioavailability that is 50-70% greater than that exhibited by infrequent users.

When *cannabis* is consumed orally, Δ-9-THC can enter the blood stream via the stomach and/or intestines due to its high absorption rate (octanol/water coefficient), e.g., 90% to 95%. After the first-pass through the liver, most of Δ-9-THC is either degraded in the stomach or metabolized into the respective hydroxylated and oxidation forms. Although to a lesser degree, Δ-9-THC metabolism has also been reported in other tissues such as brain, intestines, and lungs using redundant physiological processes.

The bioavailability of oral Δ-9-THC administration is on average between 4-20%. The timing to peak concentration of Δ-9-THC in (plasma) blood can vary (widely) among different individuals, e.g., from about 1 hour to about 6-7 hours, but usually take 2 to 4 hours.

During the secondary phase (Phase II) of THC metabolism, the hydroxylated and carboxylated metabolic products undergo a conjugation reaction with glucuronic acid. This process allows the glucuronide-bound THC, 11-OH-THC, and THC-COOH to become much more water-soluble, which help with distribution and elimination by urine and feces.

In some embodiments, to determine the concentrations of THC and its metabolites in blood, urine, feces, and other tissues following in vivo administration, a sample obtained from an individual is processed to release THC from glucuronide-bound THC prior to introduction of the sample onto a sensor according to the present teachings.

In many embodiments, the samples can be processed using one (or both) of the following processes: enzymatic-hydrolysis (cleaving) with Beta-glucuronidase or alkaline hydrolysis (cleaving) with sodium hydroxide (NaOH).

Figure 9:
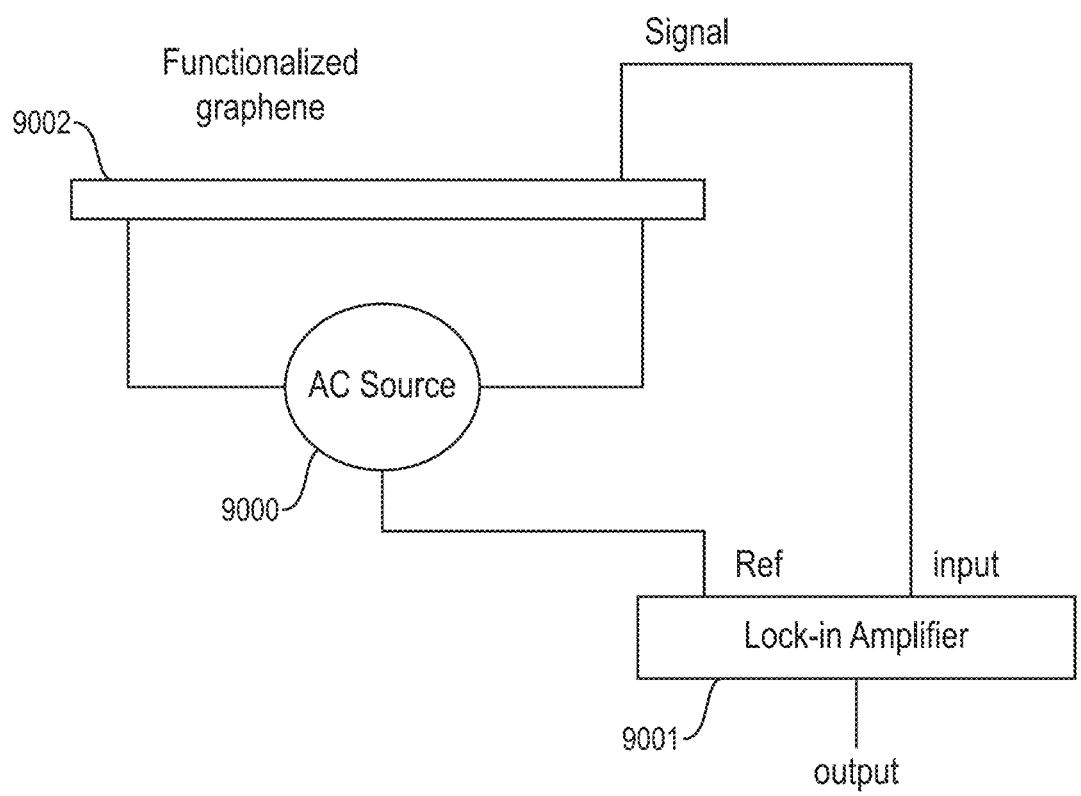
FIG. 9 schematically depicts an embodiment a system according to the present teachings.

With reference to FIG. 9, in some embodiments, an AC source 9000 can be employed to apply an AC voltage or current, e.g., with a frequency in a range of about 100 Hz to about 2 MHz, e.g., 1 kHz to 1 MHz, across an antibody-functionalized graphene layer 9002, such as a graphene layer functionalized with antibodies exhibiting specific binding to THC and/or one of its metabolites. The AC voltage or current can also provide a reference signal to a lock-in amplifier 9001 whose input port receives a signal associated with the functionalized graphene layer in response to the application of AC voltage or current (e.g., AC voltage or current depending on the signal applied to the functionalized graphene layer). The output of the lock-in amplifier can be used to determine whether THC and/or one or more of its metabolites are present in a sample under study.

In some embodiments, the graphene layer of a sensor according to the present teachings can be functionalized with an antibody fragment that exhibits specific binding to Δ-9-THC and/or one or more of its metabolites. For example, an article entitled "Antibody fragments for on-site testing of cannabinoids generated via in vitro affinity maturation," published in Bio Pharm Bull, 2017; 40(20: 174-181 by Morita et al., which is herein incorporated by reference, discloses the use of an in vitro affinity maturation technique to generate a single-chain Fv fragment (scFv) that recognizes with high affinity Δ9-tetrahydrocannabinol (THC).

In particular, Morita et al. explain that mouse monoclonal antibody against THC, Ab-THC #33, with $K_a$ 6.2×107 M−1 (as Fab fragment) was established by the hybridoma technique. Then, a "wild-type" scFv (wt-scFv) with $K_a$, 1.1×107 M−1 was prepared by bacterial expression of a fusion gene combining the $V_H$ and $V_L$ genes for Ab-THC #33. Subsequently, random point mutations in $V_H$ and $V_L$ were generated separately, and the resulting products were assembled into mutant scFv genes, which were then phage-displayed. Morita et al. further explains that repeated panning identified a mutant scFv (scFv #m1-36) with 10-fold enhanced affinity ($K_a$ 1.1×108 M−1) for THC, in which only a single conservative substitution (Ser50Thr) was present at the N-terminus of the $V_H$-complementarity-determining region 2 (CDR2) sequence. Morita et al. also indicate that in competitive enzyme-linked immunosorbent assay (ELISA), the mutant scFv generated dose-response curves with midpoint 0.27 ng/assay THC, which was 3-fold lower than that of wt-scFv. Even higher reactivity with a major THC metabolite, 11-nor-9-carboxy-Δ9-tetrahydrocannabinol, indicated that the mutant scFv will be useful for testing not only THC in confiscated materials, but also the metabolite in urine. Indeed, the antibody fragment is potentially suitable for use in advanced on-site testing platforms for cannabinoids.

In some embodiments, a sensor according to the present teachings can be functionalized with anti-cannabidiol (CBD) antibodies. In such embodiments, a graphene layer of the sensor can be functionalized with anti-CBD antibody. An example of an anti-CBD antibody suitable for use in the practice of the present teachings is marketed by Abbiotec of Escondido, Californian, under catalogue #2002223.

Figure 10:
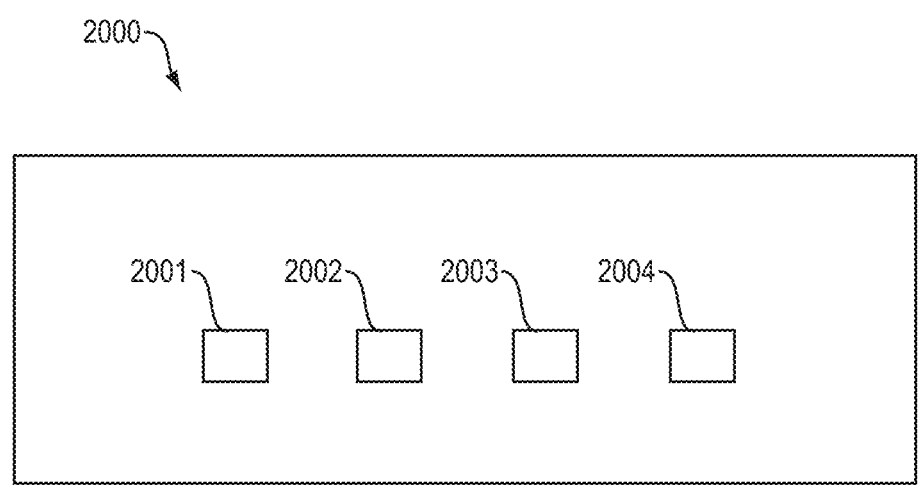
FIG. 10 depicts a sensor according to the present teachings having a plurality of sensing elements.

In some embodiments, a sensor according to the present teachings can include a plurality of graphene-based sensing elements according to the present teachings. By way of example, FIG. 10 schematically depicts such a sensor 2000 having a plurality of sensing elements 2001, 2002, 2003, and 2004. Each of the sensing elements includes a graphene layer functionalized with an anti-THC or anti-CBD antibody and has a structure similar to that discussed above in connection with sensor shown in FIG. 1 above.

In some embodiments, the signals generated by the sensing elements can be averaged to generate a resultant signal. Further, in some embodiments, at least one of the sensing elements can be configured as a calibration sensing element to allow quantification of THC and/or CBD present in a sample. By way of example, the calibration can be achieved by utilizing a calibrated sample and detecting a change in at least one electrical property of the functionalized graphene layer in response to exposure to the calibration sample.

The following example is provided for further elucidation of various aspects of the invention and is not intended to provide necessarily the optimal ways of practicing the present teachings or optical results that can be obtained.

Example

A sensor based on the design depicted in FIG. 1 was fabricated. The conductive pads were formed of silver high conductive paste purchased from MG Chemicals of Canada. The high conductive paste was employed to electrically connect the graphene layer to a measurement circuit for detecting the electrical response of the graphene layer to a test sample containing THC.

The graphene layer was functionalized with an antibody marketed by Fitzgerald Industries (#10-T43B). The functionalization process included coupling a plurality of linker molecules to the graphene layer at one end thereof and coupling the antibody molecules to the other end of the linker molecules. In this example, the linker molecule was 1-pyrenebutonic acid succinimidyl ester. The procedures for attaching the linker molecules to the graphene layer and coupling antibody molecules to the linker molecules described in U.S. Pat. No. 9,664,674, which is herein incorporated by reference in its entirety, were followed.

A sample of THC was extracted from a cartridge of an electrical cigarette available over counter. The sample was observed to be very viscous with dark yellowish color. The sample was completely dissolved in pure ethanol and was agitated in a sonicator for about 2 minutes. The solution was then diluted in TBS (Tris-buffered saline) buffer to 60%. Upon dilution, a cloudy liquid was formed. The cloudy liquid sample was then centrifuged for about 5 minutes to separate the cloudy phase and was diluted in TBS buffer 1 to 10 ratio. The clear liquid was then applied to six sensors in accordance with the following protocol.

1) A portion of the THC sample was applied to 3 sensors (Group 1).
2) An irrelevant protein, i.e., gliadin, sample prepared in TBS/Ethanol solution was applied to the other 3 sensors (Group 2).
3) The electrical resistance of the sensors in both Group 1 and Group 2 was measured.
4) The sensors in Group 2 were exposed to the THC sample for 3 minutes and the electrical measurement of the resistance was repeated for Group 2 sensors.

Figure 11:
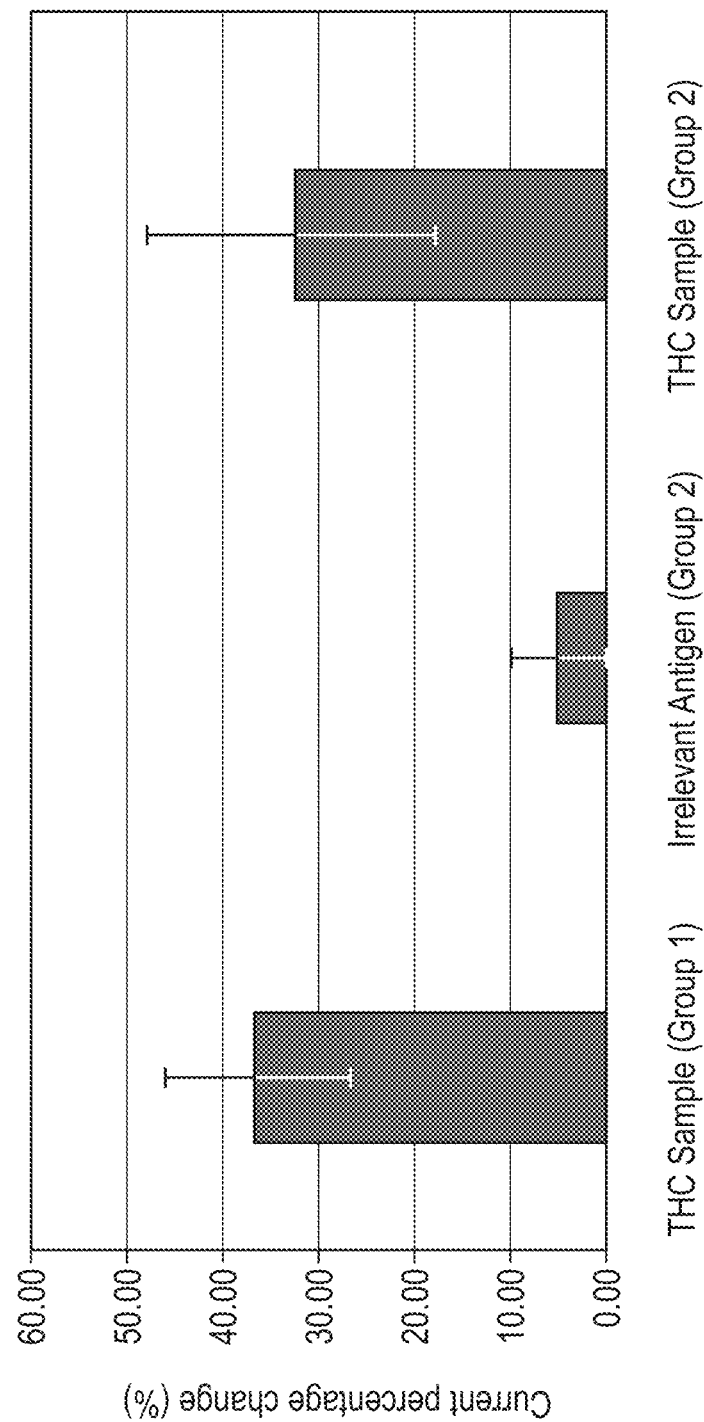
FIG. 11 presents data obtained using a prototype device according to an embodiment of the present teachings.

The electrical resistance of the sensors was monitored using a four-probe based circuit such as that described in the aforementioned U.S. Pat. No. 9,664,674 and data was recorded on the connected analyzer. FIG. 11 shows the results of the measurements in terms of percentage change in measured current when the sensors were exposed to THC and irrelevant antigen samples.

The above results show the detection of THC in the prepared sample. Further, the sensors in Group 2 exhibited low reaction to the irrelevant antigen (e.g., gliadin molecules soluble in Ethanol). The sensors in Group 2, however, exhibited a response commensurate with that observed for Group 1 sensors when they were exposed to THC samples.

Those having ordinary skill in the art will appreciate that various changes can be made to the above embodiments without departing from the scope of the invention.

What is claimed is:

1. A method of detecting tetrahydrocannabinol (THC) in a sample, comprising:
bringing a sample into contact with a graphene layer functionalized with an antibody exhibiting specific binding to THC, wherein the graphene layer consists of a monolayer of carbon atoms,
monitoring at least one electrical property of the graphene layer in response to interaction with the sample, and
detecting presence of THC in the sample by detecting a change in the electrical property indicative of interaction of THC with the anti-body functionalized graphene layer.

2. The method of claim 1, wherein the electrical property comprises an electrical resistance of the antibody-functionalized graphene layer.

3. The method of claim 1, wherein the graphene layer is disposed on an underlying substrate.

4. The method of claim 3, wherein the underlying substrate is any of semiconductor and glass.

5. The method of claim 1, wherein the graphene layer is electrically coupled to a pair of conductive pads for facilitating measurement of an electrical resistance of the graphene layer in response to interaction with the sample.

6. The method of claim 1, wherein the sample is a food sample.

7. The method of claim 1, wherein the sample is a biological sample.

8. The method of claim 7, wherein the biological sample is any of a blood, saliva and urine sample.

9. The method of claim 1, wherein the THC comprises Δ-9-THC.

10. The method of claim 1, wherein the THC comprises 11-COOH-THC.

11. The method of claim 1, wherein the THC comprises 11-OH-THC.

12. The method of claim 1, wherein the sensor exhibit a limit of detection of about 20 to about 200 ng/ml.

13. The method of claim 1, wherein the THC comprises Δ-8-THC.

14. The method of claim 1, wherein the step of monitoring the at least one electrical property comprises applying a voltage across the anti-body functionalized graphene layer and measuring a current passing through the graphene layer in response to the applied voltage.

15. The method of claim 1, wherein the step of monitoring the at least one electrical property comprises applying a current to the anti-body functionalized graphene layer and measuring a voltage across the anti-body functionalized graphene layer.

16. A system for detecting THC in a sample, comprising a sensor, comprising
 a substrate,
 a graphene layer deposited on a surface of the substrate, the graphene layer being functionalized with a plurality of antibodies exhibiting specific binding to THC, wherein the graphene-layer consists of a monolayer of carbon atoms and,
 at least one pair of electrically conductive pads coupled to the anti-body-functionalized graphene layer for measuring an electrical property of the anti-body-functionalized graphene layer.

17. The system of claim 16, wherein the electrical property comprises an electrical resistance of the antibody-functionalized graphene layer.

18. The system of claim 16, wherein the THC comprises Δ-9-THC.

19. The system of claim 16, wherein the THC comprises 11-COOH-THC.

20. The system of claim 16, wherein the THC comprises 11-OH-THC.

21. The system of claim 16, wherein the sensor exhibits a limit of detection of about 20 ng/ml to about 200 ng/ml.

22. The system of claim 16, further comprising a DC voltage or current source that applies a DC voltage or DC current to the antibody-functionalized graphene layer.

23. A method of detecting tetrahydrocannabinol (THC) in a sample, comprising:
 bringing a sample into contact with a graphene layer functionalized with an antibody exhibiting specific binding to THC, wherein the graphene-layer consists of a monolayer of carbon atoms,
 monitoring at least one electrical property of the graphene layer in response to interaction with the sample,
 detecting presence of THC in the sample by detecting a change in the electrical property indicative of interaction of THC with the anti-body functionalized graphene layer, and
 configuring a sensing element as a calibration sensing element.

24. A system for detecting THC in a sample, comprising a sensor, comprising
 a substrate,
 a graphene layer deposited on a surface of the substrate, the graphene layer being functionalized with a plurality of antibodies exhibiting specific binding to THC, wherein the graphene-layer consists of a monolayer of carbon atoms,
 at least one pair of electrically conductive pads coupled to the anti-body-functionalized graphene layer for measuring an electrical property of the anti-body-functionalized graphene layer; and
 a sensing element configured as calibration sensing element.

* * * * *